(12) United States Patent
Bunick et al.

(10) Patent No.: US 8,383,159 B2
(45) Date of Patent: Feb. 26, 2013

(54) DOSAGE FORMS HAVING A MICRORELIEFED SURFACE AND METHODS AND APPARATUS FOR THEIR PRODUCTION

(75) Inventors: Frank J. Bunick, Randolph, NJ (US); Jen-Chi Chen, Morrisville, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 1332 days.

(21) Appl. No.: 11/236,038

(22) Filed: Sep. 27, 2005

(65) Prior Publication Data

US 2006/0088585 A1 Apr. 27, 2006

Related U.S. Application Data

(60) Provisional application No. 60/622,666, filed on Oct. 27, 2004.

(51) Int. Cl.
*A61K 9/50* (2006.01)
(52) U.S. Cl. ....................................................... 424/490
(58) Field of Classification Search .................... None
See application file for complete search history.

(56) References Cited

U.S. PATENT DOCUMENTS

| | | | |
|---|---|---|---|
| 1,475,430 A | 11/1923 | Curwen |
| 4,128,658 A | 12/1978 | Price et al. |
| 4,173,626 A | 11/1979 | Dempski et al. |
| 4,455,039 A | 6/1984 | Weitzen et al. |
| 4,543,320 A | 9/1985 | Vijan |
| 4,548,825 A | 10/1985 | Voss et al. |
| 4,643,894 A | 2/1987 | Porter et al. |
| 4,668,523 A | 5/1987 | Begleiter |
| 4,675,188 A | 6/1987 | Chu |
| 4,683,256 A | 7/1987 | Porter et al. |
| 4,725,111 A | 2/1988 | Weitzen et al. |
| 4,725,441 A | 2/1988 | Porter et al. |
| 4,802,924 A | 2/1989 | Woznicki et al. |
| 4,820,524 A | 4/1989 | Berta |
| 4,828,841 A | 5/1989 | Porter et al. |
| 4,851,226 A | 7/1989 | Julian et al. |
| 4,863,742 A | 9/1989 | Panoz |
| 4,867,983 A | 9/1989 | Berta |
| 4,880,636 A | 11/1989 | Franz |
| 4,900,111 A | 2/1990 | D'Amato et al. |
| 4,906,478 A | 3/1990 | Valentine et al. |
| 4,921,319 A | 5/1990 | Mallik |
| 4,933,120 A | 6/1990 | D'Amato et al. |
| 4,966,771 A | 10/1990 | Berta |
| 4,980,170 A | 12/1990 | Schneider et al. |
| 4,984,240 A | 1/1991 | Keren-Zvi et al. |
| 5,000,388 A | 3/1991 | D'Amato |
| 5,006,362 A | 4/1991 | Hilborn |
| 5,044,707 A | 9/1991 | Mallik |
| 5,071,597 A | 12/1991 | D'Amato et al. |
| 5,075,114 A | 12/1991 | Roche |
| 5,083,850 A | 1/1992 | Mallik et al. |
| 5,089,270 A | 2/1992 | Hampton et al. |
| 5,128,779 A | 7/1992 | Mallik |
| 5,146,730 A | 9/1992 | Sadek et al. |
| 5,213,738 A | 5/1993 | Hampton et al. |
| 5,272,137 A | 12/1993 | Blase et al. |
| 5,275,822 A | 1/1994 | Valentine et al. |
| 5,286,497 A | 2/1994 | Hendrickson et al. |
| 5,374,659 A | 12/1994 | Gowan, Jr. |
| 5,393,099 A | 2/1995 | D'Amato |
| 5,405,642 A | 4/1995 | Gilis et al. |
| 5,435,840 A | 7/1995 | Hilborn |
| 5,459,983 A | 10/1995 | Sadek et al. |
| 5,468,561 A | 11/1995 | Cho |
| 5,489,436 A | 2/1996 | Hoy et al. |
| 5,489,936 A | 2/1996 | Appel et al. |
| 5,538,674 A | 7/1996 | Nisper et al. |
| 5,543,370 A | 8/1996 | Sigl et al. |
| 5,630,871 A | 5/1997 | Jordan |
| 5,658,589 A | 8/1997 | Parekh et al. |
| 5,662,732 A | 9/1997 | Kelley et al. |
| 5,827,535 A | 10/1998 | Stone |
| 5,838,466 A | 11/1998 | Mallik |
| 5,886,770 A | 3/1999 | Damato |
| 5,912,013 A | 6/1999 | Rudnic et al. |
| 6,063,404 A | 5/2000 | Timpe et al. |
| 6,103,260 A | 8/2000 | Luber et al. |
| 6,143,386 A | 11/2000 | Lorig et al. |
| 6,183,808 B1 | 2/2001 | Grillo et al. |
| 6,186,067 B1 | 2/2001 | Rorke et al. |
| 6,248,391 B1 | 6/2001 | Grillo et al. |

(Continued)

FOREIGN PATENT DOCUMENTS

| | | |
|---|---|---|
| CN | 1368890 A | 9/2002 |
| EP | 0 060 023 A | 9/1982 |

(Continued)

OTHER PUBLICATIONS

Banker et al., "tablets", from lachman, et al., Theory & Practice of Industrial Pharmacy, Chapter 11, pp. 293-345, (3$^{rd}$ Ed. 1986).

(Continued)

*Primary Examiner* — Elli Peselev
(74) *Attorney, Agent, or Firm* — William E. McGowan

(57) ABSTRACT

The present invention provides an edible dosage form that incorporates optical elements (e.g., printed patterns, microrelief gratings, and/or macrorelief gratings), capable of producing unique optical effects and images in order to enable a user to better identify and differentiate the dosage forms, as well as to improve the detection of counterfeit production thereof, wherein the edible dosage forms may be made in a variety of ways to incorporate the optical elements therein.

17 Claims, 25 Drawing Sheets

U.S. PATENT DOCUMENTS

| | | |
|---|---|---|
| 6,270,805 B1 | 8/2001 | Chen et al. |
| 6,274,162 B1 | 8/2001 | Steffenino et al. |
| 6,322,819 B1 | 11/2001 | Burnside et al. |
| 6,349,639 B1 | 2/2002 | Smith et al. |
| 6,410,213 B1 | 6/2002 | Raguin et al. |
| 6,424,467 B1 | 7/2002 | Goggins |
| 6,440,277 B1 | 8/2002 | D'Amato |
| 6,448,323 B1 | 9/2002 | Jordan et al. |
| 6,468,561 B1 | 10/2002 | Grillo et al. |
| 6,490,975 B1 | 12/2002 | Rorke et al. |
| 6,556,454 B1 | 4/2003 | D'Amato et al. |
| 6,627,212 B2 | 9/2003 | Uzunian et al. |
| 6,643,001 B1 | 11/2003 | Faris |
| 6,694,872 B1 | 2/2004 | LaBelle et al. |
| 7,083,805 B2 | 8/2006 | Begleiter |
| 2001/0050155 A1 | 12/2001 | Billiet et al. |
| 2002/0009711 A1 | 1/2002 | Wada et al. |
| 2003/0008002 A1 | 1/2003 | Uzunian et al. |
| 2003/0020179 A1 | 1/2003 | D'Amato et al. |
| 2003/0068367 A1 | 4/2003 | Sowden et al. |
| 2003/0068373 A1 | 4/2003 | Luber et al. |
| 2003/0072731 A1 | 4/2003 | Gulian et al. |
| 2003/0072799 A1 | 4/2003 | Sowden et al. |
| 2003/0086973 A1 | 5/2003 | Sowden et al. |
| 2003/0124183 A1 | 7/2003 | Sowden |
| 2003/0215585 A1 | 11/2003 | Bunick |
| 2003/0219484 A1 | 11/2003 | Sowden et al. |
| 2003/0223616 A1 | 12/2003 | D'Amato et al. |
| 2004/0109889 A1 | 6/2004 | Bunick et al. |
| 2004/0156902 A1 | 8/2004 | Lee et al. |
| 2004/0170725 A1 | 9/2004 | Begleiter |
| 2004/0175425 A1 | 9/2004 | Sowden |
| 2004/0175463 A1 | 9/2004 | Shastry et al. |
| 2005/0100499 A1 | 5/2005 | Oya et al. |
| 2005/0147724 A1 | 7/2005 | Schweinfurth |
| 2006/0068006 A1 | 3/2006 | Begleiter |
| 2008/0019925 A1* | 1/2008 | Begleiter ............... 424/10.2 |

FOREIGN PATENT DOCUMENTS

| | | |
|---|---|---|
| EP | 0 088 556 A | 9/1983 |
| EP | 0 894 495 A | 2/1999 |
| EP | 1 201 408 A2 | 5/2002 |
| EP | 1 362 582 A1 | 11/2003 |
| GB | 2 218 336 A | 11/1989 |
| JP | 6051682 A2 | 2/1994 |
| JP | 2000153543 A | 6/2000 |
| WO | WO 91/04017 A1 | 4/1991 |
| WO | WO 00/05839 A2 | 2/2000 |
| WO | WO 00/18447 A2 | 4/2000 |
| WO | WO 01/10464 A1 | 2/2001 |
| WO | WO 03/000589 A1 | 1/2003 |
| WO | WO 03/005839 A2 | 1/2003 |
| WO | WO 03/020246 A | 3/2003 |
| WO | WO 03/026628 A2 | 4/2003 |
| WO | WO 03/026630 A | 4/2003 |
| WO | WO 03/028619 A | 4/2003 |
| WO | WO 03/028990 A1 | 4/2003 |
| WO | WO 03/063616 A1 | 8/2003 |
| WO | WO 2004/073582 A2 | 9/2004 |
| WO | WO 2006/027688 A1 | 3/2006 |
| WO | WO 2006/047695 | 5/2006 |

OTHER PUBLICATIONS

Begleiter, Edible Holography: The Application of Holographic Techniques to Food Processing, SPIE Practical Holograph vol. 1461, 102-109 (1991).

Hariharan, P., Basics of Holography, pp. 79-81 (2002).

Kasper, Joseph E and Feller, Steven A, The Complete Book of Holograms: How They Work and How to Make Them, pp. 151-152 (2001).

Lake, M., "An Art Form That's Precise But Friendly Enough to Wink", New York Times [Online] URL: HTTP://WWW.DEPTHOGRAPHY.COM/TIMES.HTML (1999).

List Ph, et al. "Hager's Manual of Pharmaceutical Practice", Springer-Verlag, pp. 690-695 (1971).

Park, W. R., "Methods of Manufacture," Plastic Film Technology, Ch. 2, pp. 10-48, (1969).

Pfaff, G. and Reynders, P., "Angle-Dependent Optical Effects Deriving from Submicron Structures of Films and Pigments" 99 Chem. Rev. 1963-1981 (1999).

Rosato, et al. "Injection Molding Handbook-The Complete Molding Operation Technology, Performance, Economics", pp. 601-604, (1985).

Sales, "Light Tamers Engineered Microlens Arrays Provide New Control for Display and Lighting applications", Photonics Spectra (4 pages) (Jun. 2004).

Smith, Howard, "Principles of Holography," pp. 1-11 (1969).

Sugyama, Yoji, "Holographic composition containing Hologram Pigment", Chemical Abstracts Service, XP002397507 Abstract Database accession No. 121:121817 (1994).

USA Today (Apr. 12, 2004) Foster Klug article (www.usatoday.com).

USP 24, 2000 Version, "Official Monographs" pp. 19-20 and 856-857 (1999).

Vacca, John, "Holograms & Holography—Design, Techniques & Commercial Applications" 2001. Chapter 1: Practical Holography, Hologram Production pp. 8-10. Chapter 25: Holographic Security, pp. 532-559. Appendix F: Frequently Asked Questions, pp. 627-632.

"The Elizabeth Companies Tablet Design Training Manual" (Elizabeth Carbide Die Co., Inc., p. 7 (McKeesport, Pa).

Term: "Plastic" in Dorland's Illustrated Medical Dictionary. 2003. Retrieved Jul. 18, 2008, from http://www.credoreference.com/entry/4190986.

* cited by examiner

__US 8,383,159 B2__

DOSAGE FORMS HAVING A MICRORELIEFED SURFACE AND METHODS AND APPARATUS FOR THEIR PRODUCTION

CROSS-REFERENCE TO RELATED APPLICATION

This Application claims the benefit of U.S. Application No. 60/622,666 filed on 27 Oct. 2004, which is incorporated by reference in its entirety herein.

BACKGROUND OF THE INVENTION

1. Field of the Invention

This invention relates to composite dosage forms such as pharmaceutical compositions, and components thereof. More particularly, this invention relates to composite dosage forms comprising one or more features that provide anti-counterfeiting characteristics to the dosage forms.

2. Background Information

Dosage forms having two or more distinct portions are useful in the pharmaceutical arts for overcoming a number of commonly encountered challenges, such as, for example, including the separation of incompatible active ingredients, achieving acceptable content uniformity of a low-dose/high potency active ingredient, delivering one or more active ingredients in a pulsatile manner, and providing unique aesthetic characteristics for dosage form identification. Known methods for achieving a multi-portion pharmaceutical dosage form include particle coating, multi-layer tablets, compression-coating, and spray coating techniques. It is also known for example in the household products industry to assemble solid forms from two or more different parts for the purpose of separating active ingredients, or delivering different active ingredients at different times.

One significant opportunity in designing pharmaceutical dosage forms is that of product identification and differentiation. It is useful, both from a consumer safety perspective, and a commercial perspective, to have a pharmaceutical dosage form with a unique appearance that is readily recognizable and identifiable.

One currently used technique for providing unique dosage form identification includes the use of intagliations. Intagliations are impressed marks typically achieved by engraving or impressing a graphical representation, for example a figure, mark, character, symbol such as a letter, a name, a logo, a pictoral representation, and the like, or any combination thereof, in a tablet or other solid dosage form, such as by a punching procedure. U.S. Pat. No. 5,827,535, for example, describes soft gelatin capsules with an external surface having defined thereon an impressed graphical representation. U.S. Pat. No. 5,405,642 discloses a method of highlighting intagliations in white or colored coated tablets by spraying onto said tablets a suspension comprising a filling material having a different color, a waxy material and a solvent, then removing the solvent and the excess filling and waxy material. However, it is often difficult to maintain the waxy material in an amount sufficient to promote suitable bonding of the filling material, yet be suitably removable with solvent.

EP 088,556 relates to a method of highlighting intagliations in white or colored tablets by contacting said tablets with a dry, powdery material having a different color than that of the tablet surface, then removing the excess powdery material not deposited in the intagliations. Disadvantageously, it has been found that the adhesion of the powdery material to the intagliations is not satisfactory as the material shows a tendency to loosen and fall out.

EP 060,023 discloses a method of emphasizing intagliations in colored (i.e. not white) solid articles, in particular tablets, by coating the tablet surface and filling up the intagliations with a coating film comprising an optically anisotropic substance. An optical contrast between the tablet surface and the intagliations is obtained, presumably due to the different orientation of the optically anisotropic substance on the tablet surface and in the intagliations. However, this technique is limited to colored articles and only allows for the use of optically anisotropic filling materials.

Another way to identify and differentiate one dosage form from another is via application of microreliefs to the dosage form. See, e.g., U.S. Pat. No. 4,668,523 and WO 01/10464 (microreliefs in the outer surface of dosage form.) A microrelief is a regular pattern of ridges and grooves and the like that may display a visual effect or optical information when exposed to suitable radiant energy. Disadvantageously, production difficulties could be encountered when using these methods to stamp microrelief patterns into tablets having irregular shapes and/or surfaces.

All of the methods described above for producing a dosage form having one or more separate portions are relatively costly, complex, and time-intensive. Additionally, known methods for producing filled-in intagliations are limited in terms of suitable materials and the obtainable surface configurations and appearance of the resultant dosage form. Besides the above-mentioned limitations on the fill material itself, the tablet subcoating must be non-adhesive enough for the fill-in material to rub off upon tumbling in a hot coating pan. These methods cannot produce filled-in intagliations having the fill material raised above the tablet surface, or even perfectly flush with the tablet surface. The prior art product can only have a fill-in material surface that is slightly depressed, abraded, or concave with respect to the tablet surface.

Another significant challenge in the pharmaceutical industry is the opportunity to minimize manufacturing and packaging costs through standardization. Many drugs are available in several different strength tablets for convenience of dosing different patients with varying needs. Typically, higher strength tablets have greater weight and larger size than tablets having lower amounts of active ingredient. Handling and packaging costs could be reduced by having a dosage form design with the versatility to accommodate multiple different dosage amounts of medication in the same size tablet, yet be readily identifiable to patients and healthcare professionals in terms of identity and strength.

It would be desirable to produce an elegant dosage form having effective identification and distinguishing features using conventional manufacturing and packaging equipment.

SUMMARY OF THE INVENTION

In accordance with this invention, there is provided a dosage form comprised of, consisting of, and/or consisting essentially of at least one active ingredient, a first portion which comprises an exterior surface and one or more cavities defining at least one interior surface, which optionally may have indentations, and an exterior surface, and a second molded portion which is inlaid into the cavities of the first portion and has an exterior surface. The second molded portion bears a microrelief. The first and second portions are in contact at an interface, the second portion comprises a solidified thermally responsive material, and the second portion resides substantially conformably upon the indentations. In this embodiment, the optional indentations have a depth of up to about 20 microns, and are generally used in embodiments wherein an improved, intimate contact between the thermally responsive material and the interior surface of the cavity is desired.

In another embodiment, the-second molded portion is substantially free of pores having a diameter of about 0.5 microns to about 5.0 microns.

In another embodiment, the first and second portions are in intimate contact at the interface.

In another embodiment, the first portion is a compressed tablet.

In another embodiment, the first portion is a molded tablet.

In another embodiment, the first portion comprises an intagliation and the second portion resides in the intagliation.

In another embodiment, at least one area of the exterior surface of the second portion is flush with the exterior surface of the first portion.

In another embodiment, at least one area of the exterior surface of the second portion is raised with respect to the exterior surface of the first portion. In another embodiment, at least one area of the exterior surface of the second portion is set below with respect to the exterior surface of the first portion.

In another embodiment, the first portion consists essentially of a single homogeneous layer.

In another embodiment, the second molded portion comprises at least one active ingredient.

In another embodiment, the first portion has a first color and the inlaid second portion has a second color.

In another embodiment, the first portion comprises a first active ingredient and the inlaid second portion comprises a second active ingredient which may be the same or different than the first active ingredient.

In another embodiment, the first and second portions together provide a prearranged pattern.

In another embodiment, the first portion comprises a microelectronic device.

In another embodiment, the interior surface of one or more cavities in the first portion has a draft angle having a value less than zero.

In another embodiment, the interface is substantially coextensive with the interior surface.

In another embodiment, the exterior surface of the first portion is discontinuous and the exterior surface of the second portion is continuous. In another embodiment, the exterior surface of the first portion is continuous and the exterior surface of the second portion is discontinuous.

In another embodiment of this invention, the dosage form comprises at least one active ingredient, a core having an outer surface and a shell residing on at least a portion of the core outer surface. The shell comprises a first shell portion and a second shell portion, and the second molded shell portion is inlaid into the first shell portion and bears a microrelief. The first and second shell portions are in contact at an interface. In one embodiment, the exterior surface of the first shell portion may bear a microrelief. In yet another embodiment, the microrelief in the second shell portion may be different than the microrelief in the first shell portion.

In another embodiment, the shell has an outer surface and the second molded shell portion extends from the outer surface of the core to the outer surface of the shell.

In another embodiment, the first and second shell portions are both discontinuous.

In another embodiment, the first shell portion is discontinuous, and the second shell portion is continuous.

In another embodiment, the first shell portion has a first color and the second shell portion has a second color.

In another embodiment, the core comprises a compressed powder.

In another embodiment, the core comprises an insert.

In another embodiment, the insert comprises an active ingredient.

In another embodiment, one or more of the core, the inlaid portion or the insert comprise an active ingredient.

In another embodiment, the core comprises a microelectronic device.

In another embodiment, the insert comprises a microelectronic device.

In another embodiment, either the first shell portion, second shell portion, or both have a textured outer surface. By "textured," it is meant that the size of the indentations and protrusions on the surface are an average of at least about 20 microns.

In another embodiment, the outer surface of the shell contains a prearranged pattern.

In another embodiment, the shell comprises one or more openings therein.

In another embodiment, the outer surface of the shell is substantially smooth.

In another embodiment, the shell contains indentations, letters, symbols or a pattern.

In another embodiment, the first shell portion contains indentations, letters, symbols or a pattern.

In another embodiment, the second shell portion contains indentations, letters, symbols or a pattern.

In another embodiment, the first shell portion, second shell portion or both contain raised protrusions in the form of letters, symbols or a pattern.

In another embodiment, the inlaid portion is substantially free of pores having a diameter of about 0.5 microns to about 5.0 microns.

In another embodiment, the second shell portion has a portion thereof having a draft angle having a value less than zero at the interface.

In another embodiment of this invention, the dosage form comprises at least one active ingredient, a core, and a shell having a first molded shell portion which is discontinuous, and a second molded shell portion which is continuous and which bears a microrelief, such that the discontinuities of the first shell portion are due to the presence of the second molded shell portion, and the first and second shell portions are compositionally different.

In another embodiment, the first and second shell portions comprise a solidified thermoplastic material.

In another embodiment, the exterior surfaces of the first and second shell portions are collinear.

In another embodiment, the second molded portion has a portion thereof having a draft angle having a value less than zero.

In another embodiment, the cavities define a plurality of side walls for receiving the inlaid portion, and the side walls have a draft angle having a value less than zero.

In another embodiment, either the first portion, the second portion, or both contain an active ingredient.

Yet another embodiment is directed to a composition comprised of, consisting of, and/or consisting essentially of polymeric film flakes having at least one surface; and a carrier for the flakes, wherein the polymeric film flakes possess a microrelief on the at least one surface.

In accordance with this invention, there are also provided dosage forms, as well as methods for their production and apparatus used in their production, as set forth in the attached claims.

BRIEF DESCRIPTION OF THE DRAWINGS

FIG. 11C is an enlarged, cross-sectional side view of the dosage form.

DETAILED DESCRIPTION OF THE INVENTION

Figure 1A:
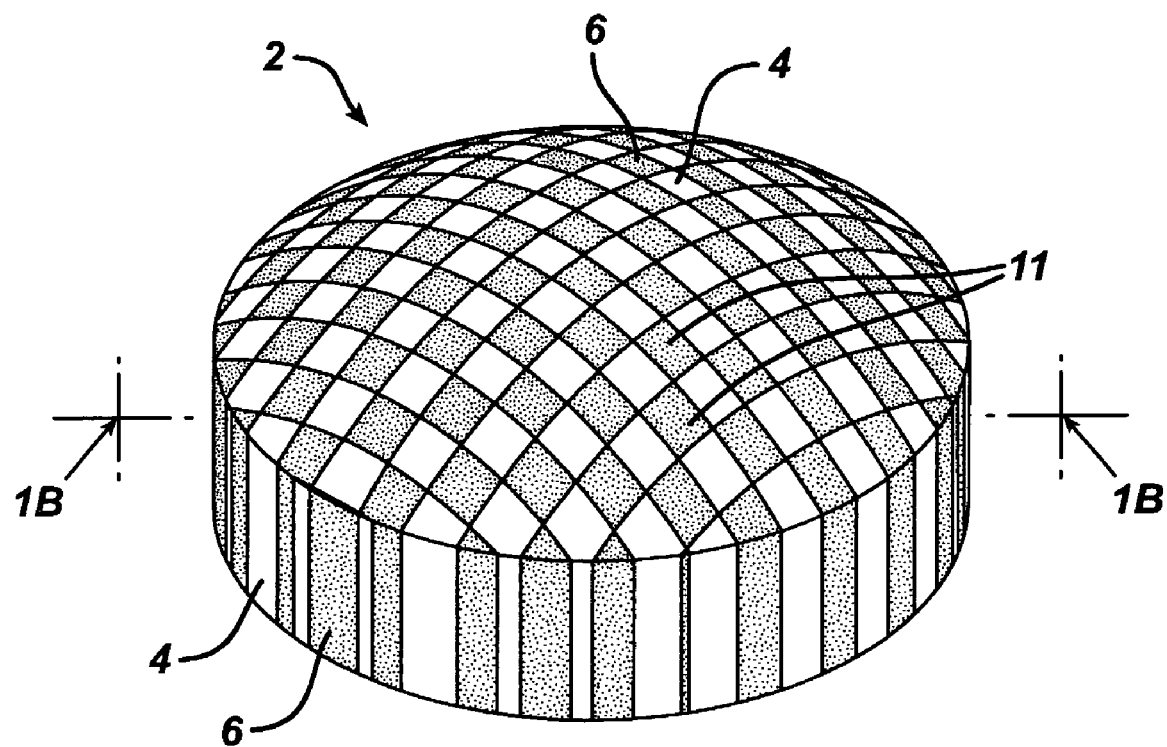
FIG. 1A depicts an example of a dosage form of this invention containing a raised microrelief in the inlaid portion.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As used herein, "structured surfaces" may include any microreliefs and/or macroreliefs.

As used herein, "microrelief," or "diffraction relief" means a regular pattern of ridges 530 and grooves or gaps 531, microstructures, and the like that may display a visual effect or optical information, covert or visible, to the human eye when exposed to suitable radiant energy. See e.g. FIG. 6B. Examples of suitable radiant energy include, but are not limited to, normal illumination, i.e., e.g., incandescent and/or daylight, and/or special illumination, e.g. laser, and/or selected wavelenghts. Microreliefs include both (1) patterns of microstructures or patterns of ridges and grooves produced through laser light interference and with other known techniques that can be subsequently transferred to a dosage form via, for example, molding, stamping or hot-embossing; and (2) "holograms," meaning, for example, the visual information, effects, and images produced by these patterns of ridges and grooves when supplied with light. Holograms shall include the product of optical images, effects, and information on the dosage form, as well as their reconstruction via the use of either white, incoherent light or laser light.

The microrelief should be "stable," which means that it has a high resistance to degradation at high temperatures, e.g., temperatures greater than about 70° C., and to changes in shape (in terms of microns) due to applied mechanical forces. The microrelief should also not affect the efficacy of the pharmaceutical active ingredient, and should be economically compatible with current dosage form production equipment.

In one embodiment, the microrelief may be a "high resolution diffraction grating," meaning one that can diffract light and has at least about 100 lines per mm, e.g., from about 100 lines per mm to about 5000 lines per mm or about 100 lines per mm to about 2000 lines per mm, or about 200 lines per mm to about 1000 lines per mm. In this embodiment, the dimensions of the diffraction relief are proportional to the wavelength of light with which is it to interact. Exemplary information that may be recorded and conveyed by this microrelief may be color, depth, image, optical data, auditory data, and/or a kinetic effect.

In another embodiment, the microrelief may be a "dovid," which is a diffractive optical variable image device, such as a hologram.

In yet another embodiment, the microrelief may be a "microetching," which is a structured surface that conveys information that is not visible to the human eye without the additional assistance of, for example magnification, i.e., e.g. at least about 100 times, or at least about 250 times, or at least about 100,000 times.

By contrast, "macroreliefs" as disclosed herein are similar in structure to microrelief gratings, but they function in a different way. In general, macroreliefs contain at least about 3 lines or "lenticules" per mm, i.e., e.g., from about 1 line per mm to about 10 lines per mm. As shown in, for example, FIG. 10, each lenticule may be a raised, curved ridge 920.

Different types of "macroreliefs," may be used in the present invention, and each type of macrorelief conveys different visual effects or animations. The simplest animation is referred to as a "lenticular flip image," which is an animation wherein one image changes to another. A lenticular flip generally allows up to three separate images to be combined and viewed independently when viewed at different angles. Another type of macrorelief is the "lenticular 3D image," which is an animation that creates apparent depth on a flat surface image and typically requires about twelve images of the subject matter arranged in a horizontal, sequential manner. A "lenticular morph image" produces the effect of gradually changing one image into another through the use of multiple images generated via sophisticated computer algorithms. "Lenticular zoom imaging" produces the effect of an image's appearing to move closer or farther away in a series of animated positions, while "lenticular full motion video imaging" displays movement using multiple frames of a coherent action sequence. Any two or more of the above type of effects or animations may be combined to produce a "lenticular combination image."

Figure 13A:
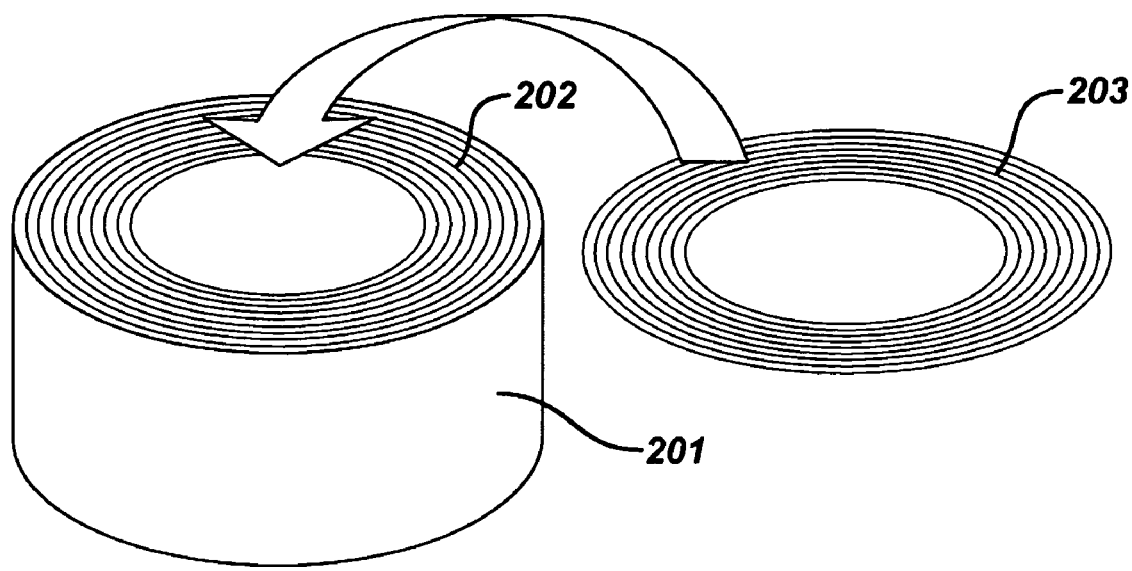
FIG. 13A is an enlarged, simplified perspective view of a dosage form printed with a first pattern, and a separate film having a second pattern that is suitable for covering the top surface of the dosage form.
Figure 13B:
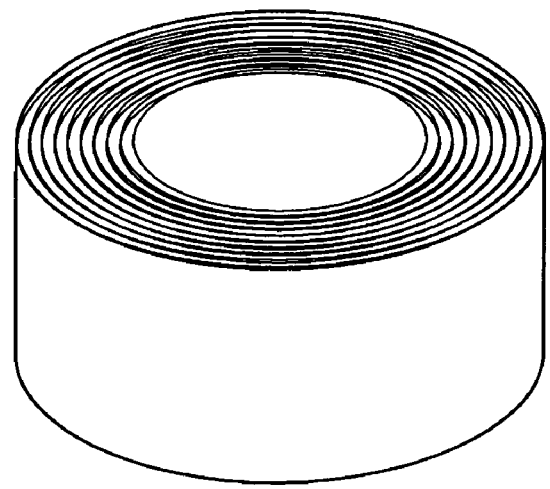
FIG. 13B is an enlarged, simplified perspective view of the dosage form resulting from covering the dosage form of FIG. 13A with the additional film of FIG. 13A to yield a dosage form having a Moiré effect.

As used herein, "Moiré" shall mean the effect produced when two or more identical, repetitive patterns of lines, circles, or array of dots are overlapped with imperfect alignment as shown in, for example, FIG. 13B.

As used herein, "injection molding" shall mean a process of forming a dosage form in a desired shape and size wherein a flowable material, which is in a fluid or flowable state form, enters a mold, then is solidified in the mold via a change in temperature (either positive or negative) before being removed therefrom. By contrast, "compression," as used herein, shall mean a process of forming a dosage form in a desired shape and size wherein a material is compacted into a tablet between the surfaces of punches via an increase in pressure before being removed therefrom.

As used herein, an "exterior surface" of a portion is a surface that comprises part of the exterior surface of the finished dosage form.

As used herein, the term "substantially conformably" refers to the fact that the cavities of the first portion are defined by surfaces having peaks and valleys therein, and the second portion resides in the cavities and the second portion also has peaks and valleys in its surfaces, such that the peaks and valleys of the surfaces of the second portion correspond substantially inversely to the major peaks and valleys of the surfaces defined by the cavities.

As used herein, the term "compositionally different" means having features that are readily distinguishable by qualitative or quantitative chemical analysis, physical testing, or visual observation. For example, the first and second materials may contain different ingredients, or different levels of the same ingredients, or the first and second materials may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

As used herein, the term "dosage form" applies to any ingestible forms, including confections. In one embodiment, dosage forms are solid, semi-solid, or liquid compositions designed to contain a specific pre-determined amount (i.e. dose) of a certain ingredient, for example an active ingredient as defined below. Suitable dosage forms may be pharmaceutical drug delivery systems, including those for oral administration, buccal administration, rectal administration, topical, transdermal, or mucosal delivery, or subcutaneous implants, or other implanted drug delivery systems; or compositions for delivering minerals, vitamins and other nutraceuticals, oral care agents, flavorants, and the like. In one embodiment, the dosage forms of the present invention are considered to be solid; however, they may contain liquid or semi-solid components. In another embodiment, the dosage form is an orally administered system for delivering a pharmaceutical active ingredient to the gastro-intestinal tract of a human. In yet another embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient.

"Active ingredients," as used herein, includes, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient may be selected from analgesics, anti-inflammatories, and antipyretics: e.g. non-steroidal anti-inflammatory drugs (NSAIDs), including propionic acid derivatives: e.g. ibuprofen, naproxen, ketoprofen and the like; acetic acid derivatives: e.g. indomethacin, diclofenac, sulindac, tolmetin, and the like; fenamic acid derivatives: e.g. mefanamic acid, meclofenamic acid, flufenamic acid, and the like; biphenylcarbodylic acid derivatives: e.g. diflunisal, flufenisal, and the like; and oxicams: e.g. piroxicam, sudoxicam, isoxicam, meloxicam, and the like. In one embodiment, the active ingredient is selected from propionic acid derivative NSAID: e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active ingredient may be selected from pseudoephedrine, phenylpropanolamine, chlorpheniramine, dextromethorphan, diphenhydramine, astemizole, terfenadine, fexofenadine, loratadine, desloratidine, doxilamine, norastemizole, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient or ingredients are present in the dosage forms of the present invention in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. In one embodiment, the dosage form comprises at least about 85 weight percent of the active ingredient.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If the active ingredient is in form of particles, the particles (whether coated or uncoated) typically have an average particle size of about 1 micron to about 2000 microns. In one embodiment, such particles are crystals having an average particle size of about 1 micron to about 300 microns. In yet another embodiment, the particles are granules or pellets having an average particle size of about 50 microns to about 2000 microns, e.g. from about 50 microns to about 1000 microns or from about 100 microns to about 800 microns.

In certain embodiments in which modified release of the active ingredient is desired, the active ingredient may optionally be coated with a known release-modifying coating. This advantageously provides an additional tool for modifying the release profile of active ingredient from the dosage form. For example, the dosage form may contain coated particles of one or more active ingredients, in which the particle coating confers a release modifying function, as is well known in the art. Examples of suitable release modifying coatings for particles are described in U.S. Pat. Nos. 4,173,626; 4,863,742; 4,980,170; 4,984,240; 5,286,497; 5,912,013; 6,270,805; and 6,322,819. Commercially available modified release active ingredients may also be employed. For example, acetaminophen particles, which are encapsulated with release-modifying polymers by a coaccervation process, may be used in the present invention. Such coaccervation-encapsulated acetaminophen is commercially available from, for example, Eurand America, Inc. or Circa Inc. If the active ingredient has an objectionable taste, and the dosage form is intended to be chewed or disintegrated in the mouth prior to swallowing, the active ingredient may be coated with a taste masking coating, as known in the art. Examples of suitable taste masking coatings are described in, for example, U.S. Pat. Nos. 4,851,226; 5,075,114; and 5,489,436. Commercially available taste masked active ingredients may also be employed. For example, acetaminophen particles, which are encapsulated with ethylcellulose or other polymers by a coaccervation process, may be used in the present invention. Such coaccervation-encapsulated acetaminophen is commercially available from Eurand America, Inc. or Circa Inc.

The active ingredient or ingredients are typically capable of dissolution upon contact with a fluid such as water, stomach acid, intestinal fluid or the like. In one embodiment, the dissolution characteristics of the active ingredient meet USP specifications for immediate release tablets containing the active ingredient. In embodiments in which it is desired for the active ingredient to be absorbed into the systemic circulation of an animal, the active ingredient or ingredients should be capable of dissolution upon contact with a fluid such as water, gastric fluid, intestinal fluid or the like. In one embodiment, the dissolution characteristics of the active ingredient meet USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the active ingredient may be modified: e.g. controlled, sustained, extended, retarded, prolonged, or delayed.

In general, one embodiment of the present invention creates dosage forms having at least one filled-in, molded intagliation or cavity portion bearing a microrelief. These microreliefs may be formed in the filled-in, molded intagliation portion via stamping, etching, or molding using high-volume, high-speed dosage form production methods and apparatus. The active ingredient may be in the core, the filled in portions, and/or any coatings applied onto the dosage form.

In one embodiment, the container in which the dosage form is carried, or the packaging therefor, may also contain a component, such as a cap, flap, sidewall, or the like, that facilitates special illumination, e.g., a polarizing filter element or a color filter element.

The dosage forms may contain at least one active ingredient, a first portion, which comprises one or more cavities, which optionally may further contain indentations on the cavity surface, and an exterior surface, and a second molded portion, which is inlaid into the cavities of the first portion and has an exterior surface. The first and second portions are in contact at an interface, the second portion comprises a solidified thermoplastic material bearing a microrelief, and the second portion resides substantially conformably upon the indentations of the first portion.

Alternatively, the dosage forms may contain at least one active ingredient, a core having an outer surface and a shell residing on at least a portion of the core outer surface, wherein the shell comprises a first shell portion and a second shell portion, and the second molded shell portion, which is inlaid into the first shell portion, bears a microrelief.

In yet another embodiment of this invention, the dosage form may contain at least one active ingredient, a core, and a shell having a first molded shell portion which is discontinuous, and a second molded shell portion which is continuous and which bears a microrelief, such that the discontinuities of the first shell portion are due to the presence of the second molded shell portion, and the first and second shell portions are compositionally different. In another embodiment, the first molded shell portion is continuous and the second molded shell portion, which bears a microrelief, is discontinuous.

In yet another embodiment of this invention, the dosage form may contain at least one active ingredient, a core, and a shell having a first molded shell portion which is continuous, and a second molded shell portion which is discontinuous and which bears a microrelief, such that the discontinuities of the second shell portion are due to the presence of the first shell portion, and the first and second shell portions are compositionally different.

In certain embodiments, the first portion consists essentially of a single homogeneous layer. In other words, it may be a single molded composition (e.g. core or stripe) or a single compressed tablet. If the portion were divided into parts, each part would have the same density, porosity, color, crystallinity, etc.

In embodiments in which the first portion is prepared via compression, suitable excipients include, but are not limited to, fillers, binders, disintegrants, lubricants, glidants, and the like.

In embodiments in which the first portion is prepared via compression, suitable fillers include, but are not limited to, water-soluble compressible carbohydrates such as sugars, which include dextrose, sucrose, isomaltalose, fructose, maltose, and lactose, polydextrose, sugar-alcohols, which include mannitol, sorbitol, isomalt, maltitol, xylitol, erythritol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

In embodiments in which the first portion is prepared via compression, suitable binders include, but are not limited to, dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and derivatives and mixtures thereof.

In embodiments in which the first portion is prepared via compression, suitable disintegrants include, but are not limited to, sodium starch glycolate, cross-linked polyvinylpyrrolidone, cross-linked carboxymethylcellulose, starches, microcrystalline cellulose, and the like.

In embodiments in which the first portion is prepared via compression, suitable lubricants include, but are not limited to, long chain fatty acids and their salts, such as magnesium stearate and stearic acid, talc, and waxes.

In embodiments in which the first portion is prepared via compression, suitable glidants include, but are not limited to, colloidal silicon dioxide, and the like.

In embodiments in which the first portion is prepared via compression, the dosage form of the invention may also incorporate pharmaceutically acceptable adjuvants, including, but not limited to preservatives, high intensity sweeteners such as aspartame, acesulfame potassium, cyclamate, saccharin, sucralose, and the like; and other sweeteners such as dihydroalcones, glycyrrhizin, Monellin™, stevioside, Talin™, and the like; flavors, antioxidants, surfactants, and coloring agents.

Figure 1B:
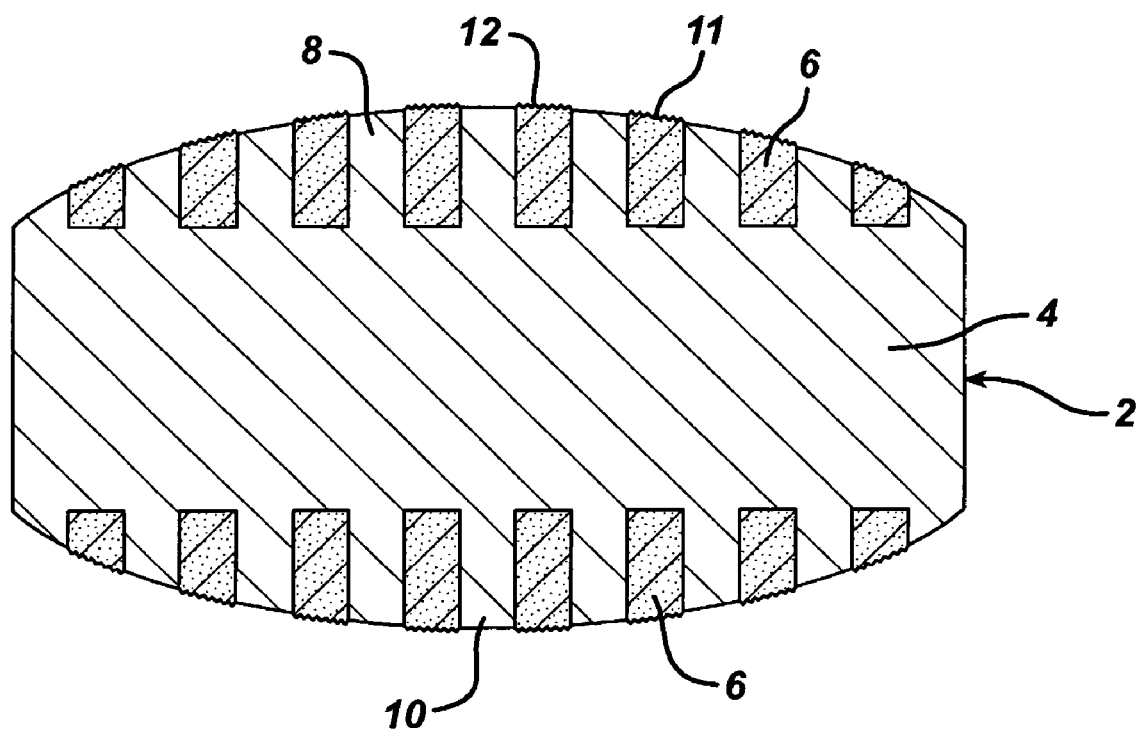
FIG. 1B depicts a cross-sectional view thereof.

An overall understanding of the dosage form of this invention may be obtained by reference to FIGS. 1A, 1B, 2A and 2B. FIGS. 1A and 1B depict one embodiment of the dosage form of this invention. In FIG. 1A, a dosage form 2 is depicted which comprises a first portion 4. The first portion comprises a plurality of debossments or cavities, which in turn comprise inlaid second portions 6. The exterior surfaces of one or more of the second portions 6 possess a microrelief 11. In this embodiment, a first active ingredient may be located within first portion 4 and an optional second active ingredient may be located within inlaid second portions 6, although in other embodiments only one of inlaid second portions 6 or first portion 4 may contain an active ingredient.

The flowable material used in the second portions 6 bearing a microrelief 11 must be able to retain a fine micrograph pattern, when exposed to humidity and temperature variations typically encountered during storage, shipment, and use of the dosage forms worldwide. In addition, these flowable materials should easily and cleanly release from the mold or stamp change part, without damaging the microrelief, after the dosage form has cooled and set.

Figure 1C:
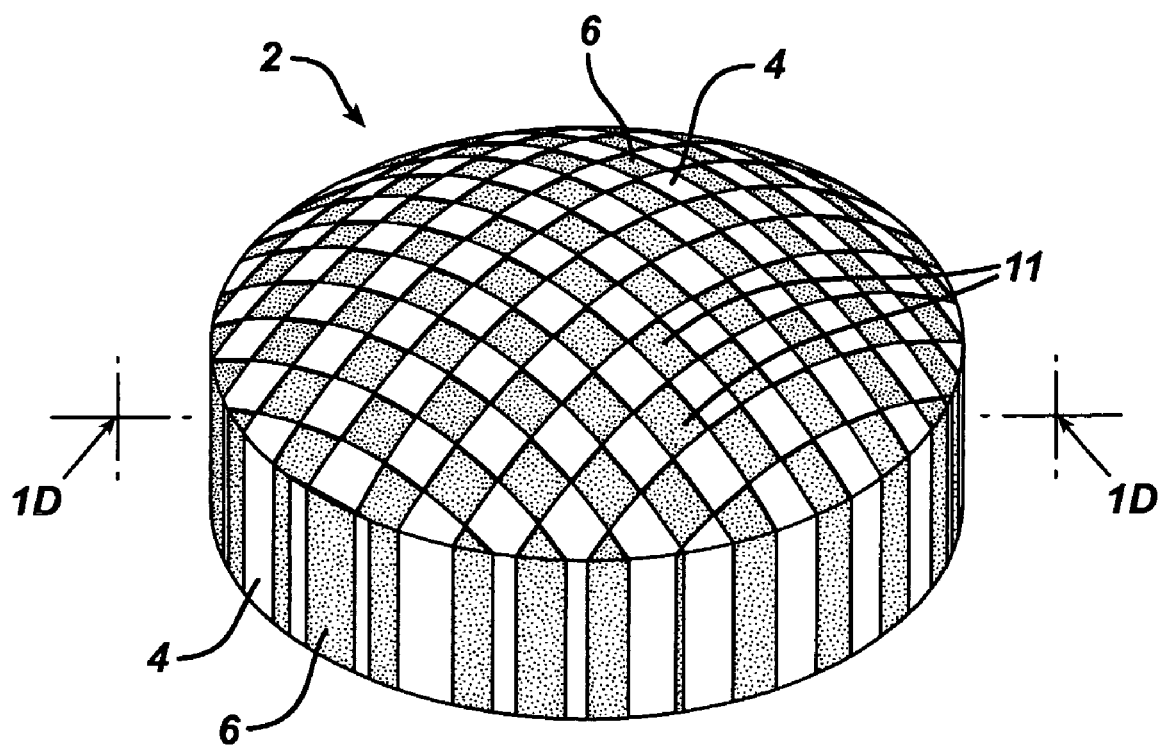
FIG. 1C depicts an example of a dosage form of this invention containing a recessed microrelief in the inlaid portion.
Figure 1D:
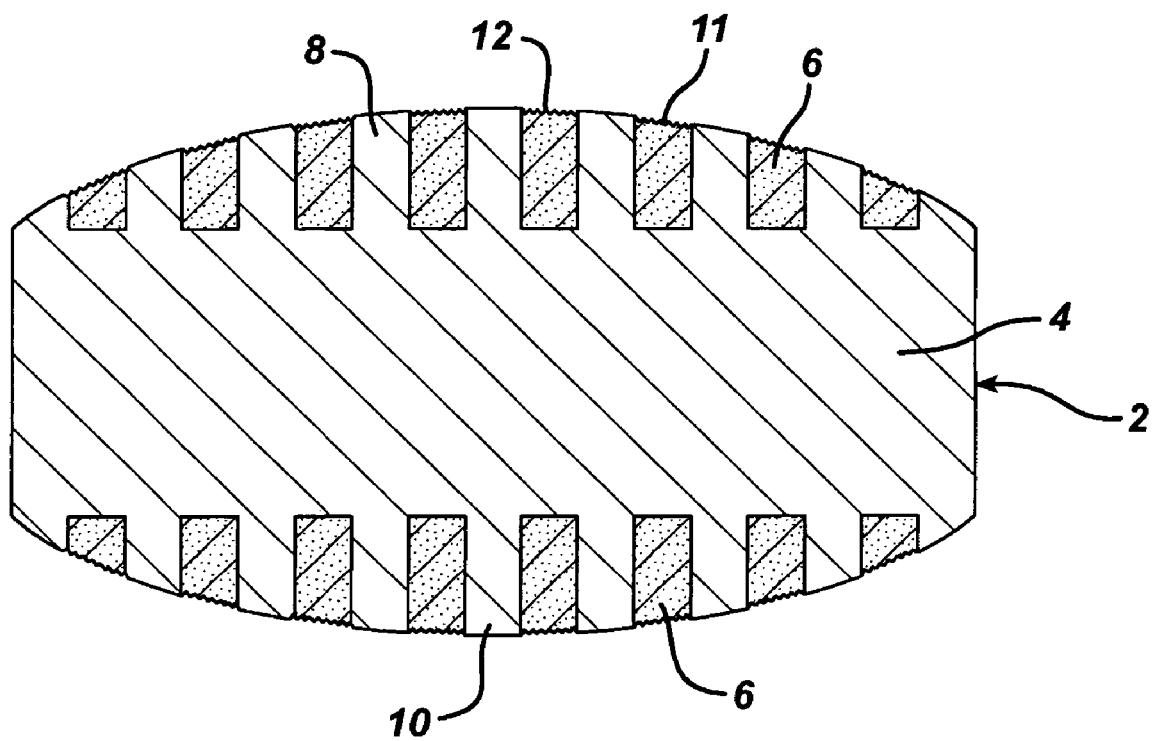
FIG. 1D depicts a cross-sectional view thereof.

FIG. 1B is a cross-sectional view of the dosage form 2 of FIG. 1A. As shown in FIG. 1B, inlaid second portions 6 may extend partially into the first portion 4 from both first upper or top surface 8 and second lower or bottom surface 10. As shown, portions of the microreliefs 11 may be raised and protrude above the first surface 8 and the second surface 10 of the first portion 4. Alternatively, as shown in FIG. 1C and FIG. 1D, the microreliefs 11 may alternatively be recessed and extend partially into the first surface 8 or second surface 10. Although not shown, the tips or ridges 12 of the microreliefs 11 may also be at approximately the same level as the surface of the proximate first surface 8 or second surface 10. In these embodiments, a first active ingredient may be located within inlaid second portions 6 and an optional second active ingredient (which may be the same or different than the first active ingredient) may be located within first portion 4, although in other embodiments only one of inlaid second portions 6 or first portion 4 may contain an active ingredient.

In one embodiment, the first and second portions together provide a prearranged pattern. In yet another embodiment, the second portion may comprise a flavoring agent or sensate. As used herein, a "sensate" is a chemical agent that elicits a sensory effect in the mouth, nose, and/or throat other than aroma or flavor. Examples of such sensory effects include, but are not limited to, cooling, warming, tingling, mouth watering (succulent), astringent, and the like. Sensate agents suitable for use in the present invention are commercially available and may be purchased from, for example, International Flavor & Fragrances.

Figure 1E:
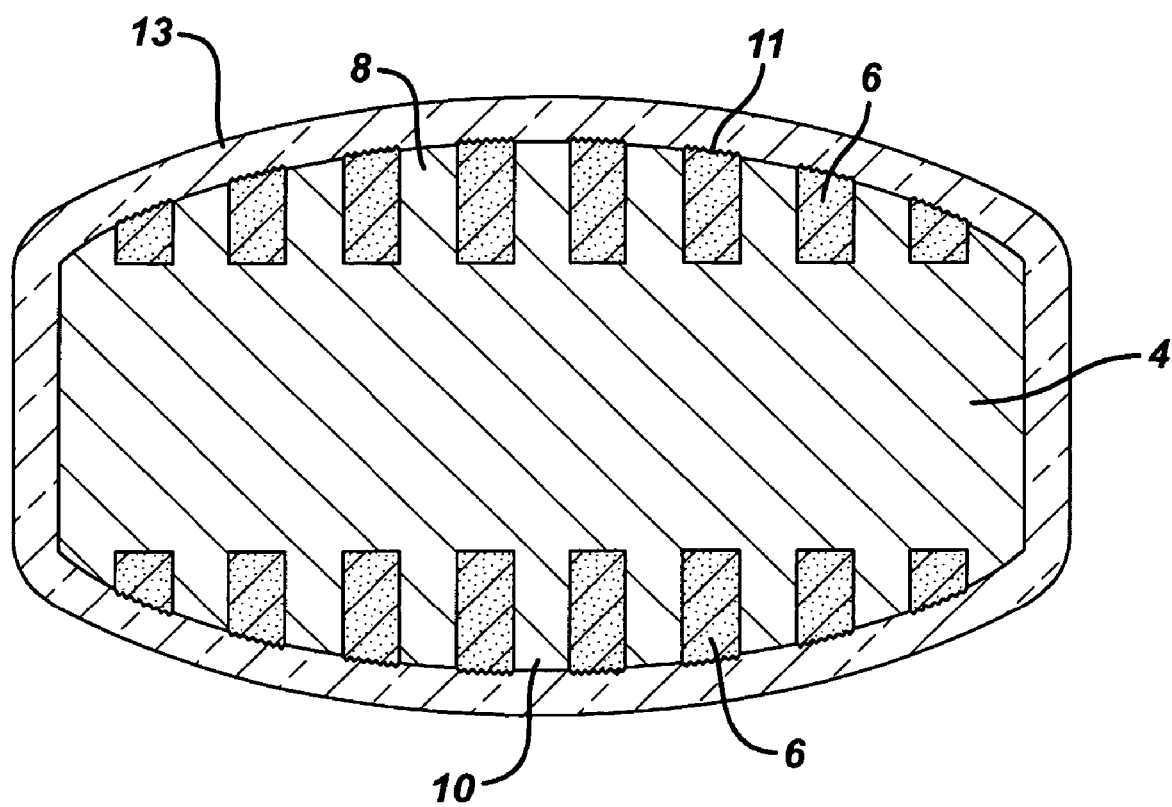
FIGS. 1E and 1F depict a cross-sectional view of the dosage form of FIGS. 1B and 1D, respectively, with an optional top coating.
Figure 1F:
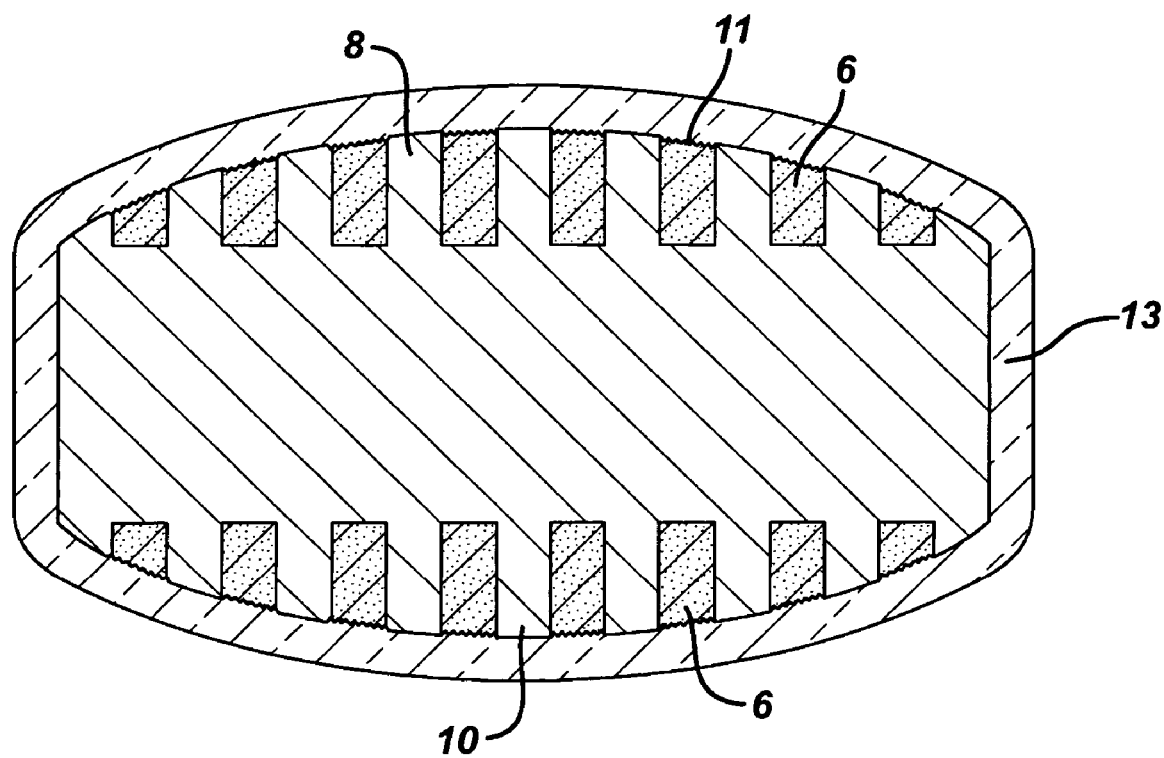

The dosage forms depicted in FIGS. 1E and 1F further contain a clear or semi-transparent top coating 13 that resides on first surface 8 and second surface 10. The top coating 13 may also partially (not shown) or fully reside on the micrograph-containing inlaid portions 6 of the dosage form.

Suitable polymers for inclusion in top coatings include polyvinylalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; polyvinylpyrrolidone and polyvinylacetate copolymers; and derivatives and combinations thereof. Suitable film-forming water insoluble polymers for inclusion in top coatings include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable film-forming pH-dependent polymers for inclusion in top-coatings include enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, "EUDRAGIT S;" and poly(methacrylic acid, methyl methacrylate) 1:1, which is commercially available from Rohm Pharma GmbH under the tradename, EUDRAGIT L; poly (butyl methacrylate (dimethylaminoethyl)methacrylate, methyl methacrylate), which is commercially available from Rohm Pharma GmbH under the tradename, "EUDRAGIT E;" and the like, and derivatives, salts, copolymers, and combinations thereof.

In one embodiment, top coating 13 includes those coatings having a high rigidity, i.e., e.g., those coatings having a yield value sufficient to prevent deformation of the microrelief when exposed to normal manufacturing, handling, shipping, storage, and usage conditions. Suitable top coatings having high rigidity include film formers, such as for example, the high tensile strength film-formers well known in the art. Examples of suitable high tensile strength film-formers include, but are not limited to methacrylic acid and methacrylate ester copolymers; polyvinylpyrrolidone; cellulose acetate; hydroxypropylmethylcellulose ("HPMC"), polyethylene oxide and polyvinylalcohol, which is commercially available from BASF under the tradename, "Kollicoat IR"; ethylcellulose; polyvinyl alcohols; and copolymers and mixtures thereof.

In one embodiment, the top coatings may include the water-soluble high rigidity film formers selected from HPMC, polyvinylpyrrolidone, the aminoalkyl-methacrylate copolymers marketed under the trade mark, "EUDRAGIT E," and copolymers and mixtures thereof.

In embodiments wherein high clarity is of particular concern, the top coatings may include the high clarity high-rigidity film formers selected from the acrylates such as the aminoalkyl-methacrylate copolymers marketed under the trademark, "EUDRAGIT E" polyvinylpyrrolidone, cellulose acetate, polyethylene oxide and polyvinylalcohol, , ethylcellulose, and polyvinyl alcohol shellac.

In general, the thickness of the top coating may range from about 50 microns to about 200 microns, and the rigidity of the locating layer will increase as the thickness is increased.

The dosage form may contain, based upon the total weight of the dosage form, from about 0.1 percent to about 10 percent of the top coating.

The top coating 13 may be applied via any means known in the art such as, for example, spray coating as disclosed in, U.S. Pat. Nos. 4,683,256, 4,543,370, 4,643,894, 4,828,841, 4,725,441, 4,802,924, 5,630,871, and 6,274,162; dip coating as disclosed in, U.S. Pat. Nos. 5,089,270; 5,213,738; 4,820,524; 4,867,983; and 4,966,771; or injection molding as disclosed in, US application 2003-0219484 A1.

Figure 2A:
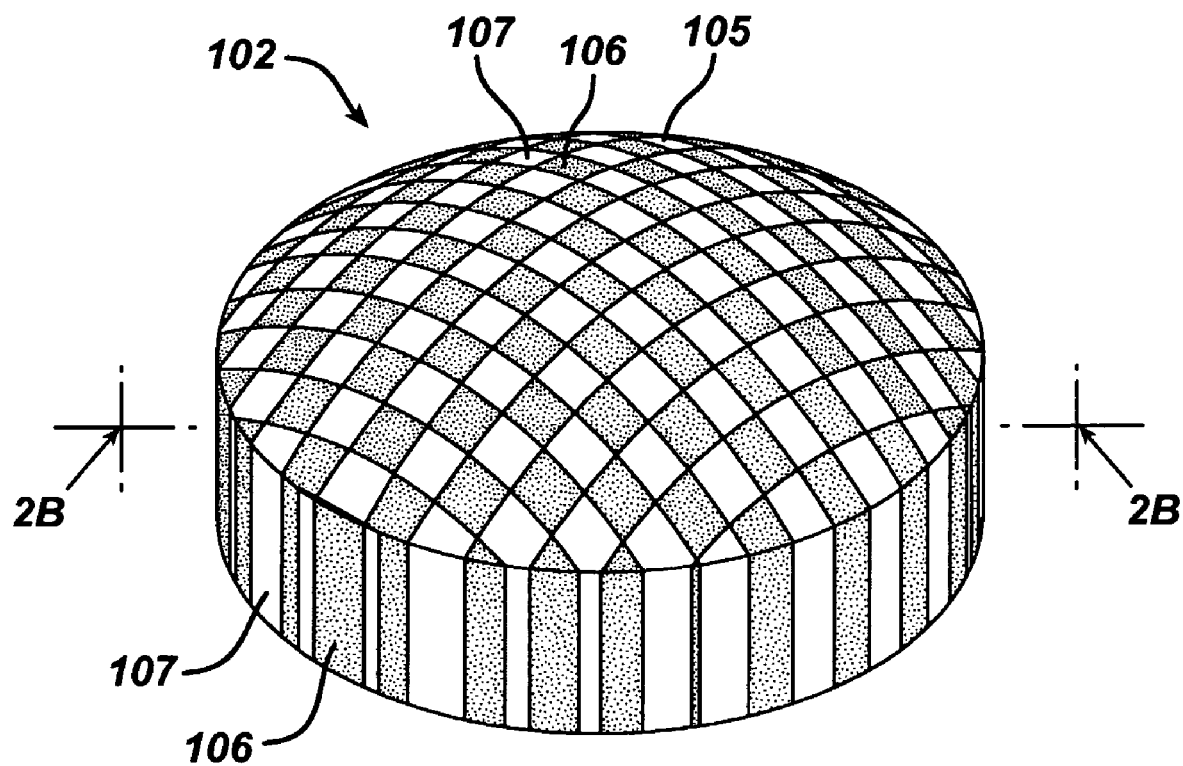
FIG. 2A depicts another example of a dosage form of this invention, in which the core has a shell residing thereon, which contains an inlaid portion.
Figure 2B:
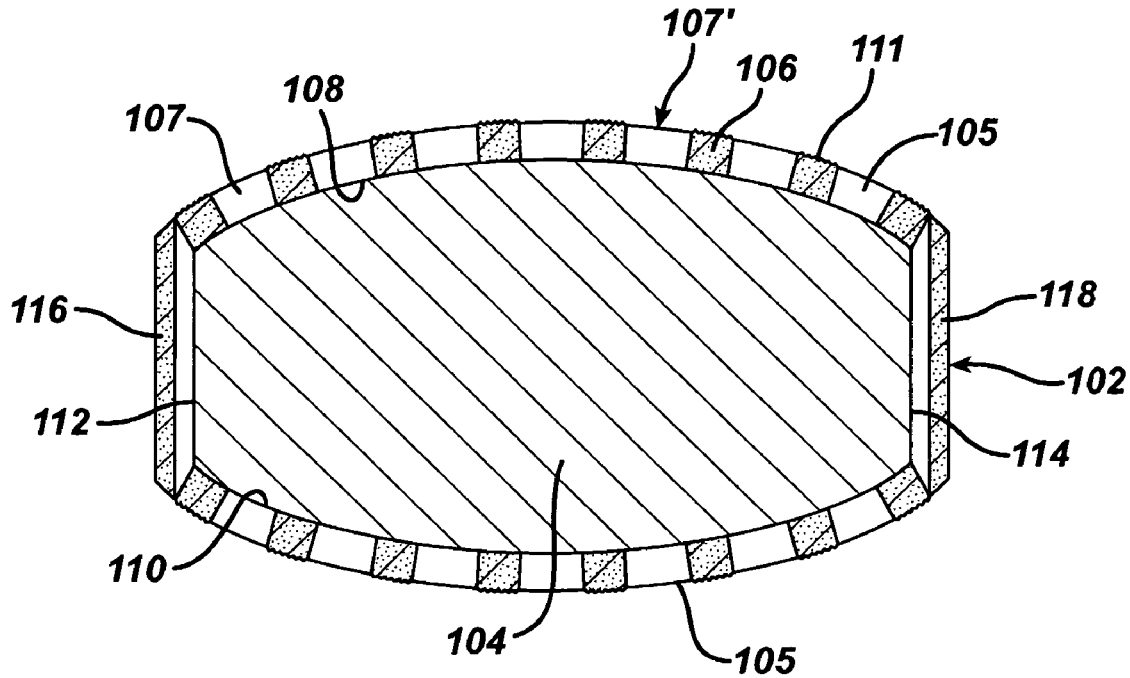
FIG. 2B depicts a cross-sectional view thereof.

In one embodiment, the refractive index of the topcoat is not equivalent to the refractive index of the core. The topcoat may also be clear or semi-transparent in FIGS. 2A and 2B depict another embodiment of this invention. FIG. 2A depicts a dosage form 102 that comprises a core 104. The core has a shell 105 residing on at least a portion of the exterior surface of core 104. The shell 105 is shown in greater detail in FIG. 2B, which is a cross-sectional view of the dosage form of FIG. 2A. As shown in FIG. 2B, the shell 105 residing on the exterior surfaces 108 and 110 of core 104 comprises a first shell portion 107 having cavities, with molded inlaid second shell portions 106 residing in the cavities. At least one of the inlaid second shell portions 106 possesses micrographs 111. These micrographs may protrude from, be substantially uniform with, or be recessed from the proximate shell portion exterior surface 107'. In this embodiment, a first active ingredient may be located within shell portion 107 and a second active ingredient may be located within inlaid second shell portions 106, although in other embodiments only one of first shell portion 107 or inlaid second shell portions 106 may contain an active ingredient. Core 104 may optionally also contain an active ingredient, which may be the same or different than the active ingredient contained in first shell portion 107 and inlaid second shell portions 106.

As depicted in FIG. 2B, the shell 105 may extend along the side portions 112 and 114 of core 104, and inlaid portions 116 and 118 may reside in the cavities of shell 105. In this embodiment, the cavities extend through the first shell portion up to the surface of the core; however, in other embodiments the cavities may only extend through a part of the first shell portion. In alternative embodiments (not shown) the cavity may extend through either a portion or all of the core.

Figure 2C:
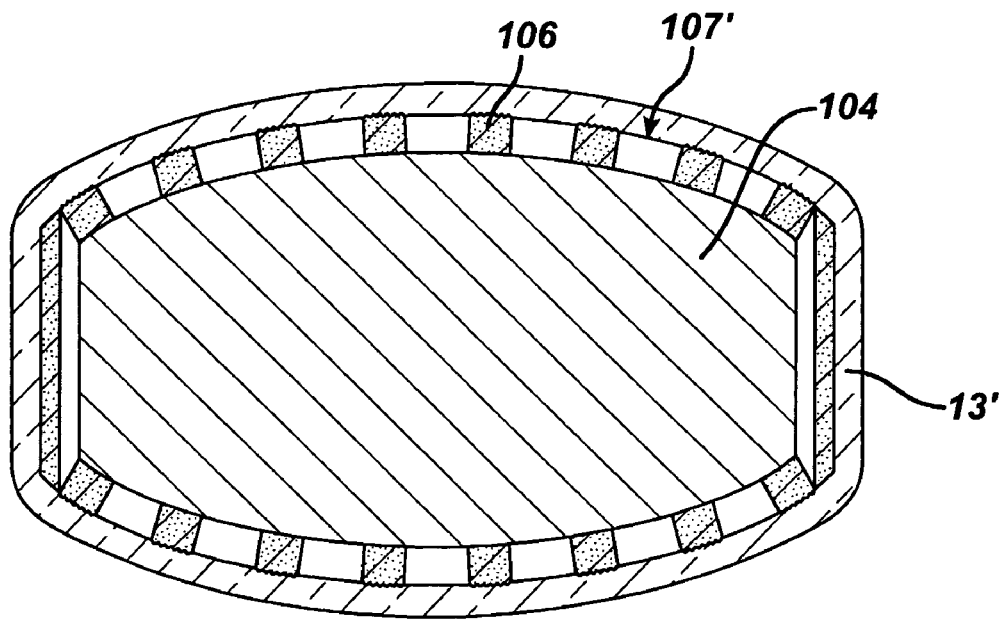
FIG. 2C depicts the dosage form of FIG. 2A with an optional top coating.

The dosage form depicted in FIG. 2C further contains a clear or semi-transparent top coating 13' that resides on the surface 107'. The top coating 13' may also partially or fully reside on the micrograph-containing inlaid portions 106 of the dosage form. Examples of suitable top coatings 13' include any of those set forth above. The dosage form of this embodiment may contain, based upon the total weight of the dosage form, from about 1 percent to about 10 percent of the top coating 13'.

The core (or substrate) may be any solid or semi-solid form. The core may prepared by any suitable method, for example the core be a compressed dosage form, or may be molded. As used herein, "substrate" refers to a surface or underlying support, upon which another substance resides or acts, and "core" refers to a material, which is at least partially enveloped or surrounded by another material. For the purposes of the suitable for use in a dosage form: i.e. the term "core" may also used to refer to a "substrate." In one embodiment, the core comprises a solid, for example, the core may be a compressed or molded tablet, hard or soft capsule, suppository, or a confectionery form such as a lozenge, nougat, caramel, fondant, or fat based composition. In certain other embodiments, the core may be in the form of a semi-solid or a liquid in the finished dosage form.

The core may be in a variety of different shapes. For example, in one embodiment the core may be in the shape of a truncated cone. In other embodiments the core may be shaped as a polyhedron, such as a cube, pyramid, prism, or the like; or may have the geometry of a space figure with some non-flat faces, such as a cone, cylinder, sphere, torus, or the like. Exemplary core shapes which may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

1. Shallow Concave.
2. Standard Concave.
3. Deep Concave.
4. Extra Deep Concave.
5. Modified Ball Concave.
6. Standard Concave Bisect.
7. Standard Concave Double Bisect.
8. Standard Concave European Bisect.
9. Standard Concave Partial Bisect.
10. Double Radius.
11. Bevel& Concave.
12. Flat Plain.
13. Flat-Faced-Beveled Edge (F.F.B.E.).
14. F.F.B.E. Bisect.
15. F.F.B.E. Double Bisect.
16. Ring.
17. Dimple.
18. Ellipse.
19. Oval.
20. Capsule.
21. Rectangle.
22. Square.
23. Triangle.
24. Hexagon.
25. Pentagon.
26. Octagon.
27. Diamond.
28. Arrowhead.
29. Bullet.
30. Barrel.
31. Half Moon.
32. Shield.
33. Heart.
34. Almond.
35. House/Home Plate.
36. Parallelogram.
37. Trapezoid.
38. FIG. 8/Bar Bell.
39. Bow Tie.
40. Uneven Triangle.

The core or sub-core may optionally be at least partially covered by a compressed, molded, or sprayed sub-coating. However, in another embodiment, the core may be substantially free of the subcoating: i.e. there is no subcoating located between the outer surface of the core and the inner surface of the shell. Any composition suitable for film-coating a tablet may be used as a subcoating according to the present invention. Examples of suitable subcoatings include, but are not limited to, those disclosed in, for example, U.S. Pat. Nos. 4,683,256, 4,543,370, 4,643,894, 4,828,841, 4,725,441, 4,802,924, 5,630,871, and 6,274,162. Additional suitable subcoatings may include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating and/or the top coating may comprise an effect pigment that acts to maximize the reflectance of the core. Examples of suitable effect pigments include, but are not limited to, platy titanium dioxide, such as that disclosed in U.S. Pat. No. 6,627,212; and transition metal oxide coated platy mica such as that commercially available from EMD Chemicals Inc. under the tradename, "CANDURIN." See also Pfaff, G. and Reynders, P., "*Angle-dependent Optical Effects Deriving from Submicron Structures of Films and Pigments,*" 99 Chem. Rev. 1963-1981 (1999). In embodiments wherein the dosage form contains a subcoating, the dosage form may contain, based upon the total weight of the dosage form, from about 1 percent to about 5 percent of the subcoating.

In embodiments wherein the core is a compressed dosage form, for example. a compressed tablet, the core may be obtained from a compressed powder. The powder may contain an active ingredient, and optionally comprise various excipients, such as binders, disintegrants, lubricants, fillers and the like, as is conventional, or the powder may comprise other particulate material of a medicinal or non-medicinal nature, such as inactive placebo blends for tableting, confectionery blends, and the like. One particular formulation comprises active ingredient, as an excipient, a plastically deforming compressible material, and optionally other excipients, such as disintegrants and lubricants and is described in more detail in United States Patent Application Publication No. 20030068373. During compression, the plastically deforming compressible material assumes the shape of the microrelief from the upper and/or lower punch surface.

Suitable plastically deforming compressible materials for these embodiments include: microcrystalline cellulose, waxes, fats, mono- and di-glycerides, derivatives and mixtures thereof, and the like. In certain embodiments, wherein the plastically deforming compressible material is later caused to melt and be absorbed into the tablet, the plastically deforming compressible material may be selected from low-melting plastically deforming compressible materials, such as plastically deforming compressible powdered waxes, such as shellac wax and microcrystalline wax, polyethylene glycol, and mixtures thereof.

The core may also optionally comprise a sub-core (which may also be referred to as an "insert"), which may be made by any method, for example compression or molding, and which may optionally contain one or more active ingredients.

In one embodiment of the invention, the dosage forms of this invention comprise a core made from a blend of powders having an average particle size of about 50 microns to about 500 microns. In one embodiment, the active ingredient has an average particle size of about 50 microns to about 500 microns. In another embodiment, at least one excipient has an average particle size of about 50 microns to about 500 microns, e.g. about 100 to about 500 microns. In one such embodiment, a major excipient, i.e. an excipient comprising at least 50% by weight of the core, has an average particle size of about 50 microns to about 500 microns, e.g. about 100 to about 500 microns. Particles in this size range are particularly useful for direct compression processes.

In one embodiment of the invention, the core may be a directly compressed tablet made from a powder that is substantially free of water soluble polymeric binders and hydrated polymers. This composition is advantageous for maintaining an immediate release dissolution profile, minimizing processing and material costs, and providing for optimal physical and chemical stability of the dosage form.

In embodiments in which the core is prepared by direct compression, the materials comprising the core, e.g. the active ingredient or ingredients and excipients, may be blended together, for example as dry powders, and fed into a cavity of an apparatus that applies pressure to form a core. Any suitable compacting apparatus may be used, including for example a roller compactor such as a chilsonator or drop roller; or a conventional tablet press. In one embodiment, the core may be formed by compaction using a rotary tablet press as known in the art. In general, a metered volume of powder is filled into a die cavity of the rotary tablet press, and the cavity rotates as part of a "die table" from the filling position to a compaction position. At the compaction position, the powder is compacted between an upper and a lower punch, then the resulting tablet is pushed from the die cavity by the lower punch. Advantageously, the direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which could have a negative effect on dissolution.

In another embodiment, the core may be prepared by the compression methods and apparatus described in United States Patent Application Publication No. 20040156902. Specifically, the core may be made using a rotary compression module comprising a fill zone, insertion zone, compression zone, ejection zone, and purge zone in a single apparatus having a double row die construction as shown in FIG. 6 of United States Patent Application Publication No. 20040156902. The dies of the compression module may then be filled using the assistance of a vacuum, with filters located in or near each die. The purge zone of the compression module includes an optional powder recovery system to recover excess powder from the filters and return the powder to the dies.

In another embodiment, the core may be prepared by a wet-granulation method, in which the active ingredient or ingredients, appropriate excipients, and a solution or dispersion of a wet binder (e.g. an aqueous cooked starch paste, or solution of polyvinyl pyrrolidone) may be mixed and granulated. Suitable apparatus for wet granulation include low shear, e.g. planetary mixers, high shear mixers, and fluid beds, including rotary fluid beds. The resulting granulated material may then be dried, and optionally dry-blended with further ingredients, e.g. adjuvants and/or excipients such as, for example, lubricants, colorants, and the like. The final dry blend is then suitable for compression by the methods described in the previous paragraph.

Methods for direct compression and wet granulation processes are known in the art, and are described in detail in, for example, Lachman, et al., *The Theory and Practice of Industrial Pharmacy*, Chapter 11 (3rd ed. 1986).

In one embodiment, the first portion or core may also be prepared by thermal setting injection molding using the method and apparatus in which the mold is maintained at approximately a constant temperature as described in United States Patent Application Publication No. 20030124183. In this embodiment, the first portion or core may be formed by injecting a starting material in flowable form into a molding chamber. The starting material may comprise an active ingredient and a thermally responsive material, which is introduced to the mold at a temperature above the glass transition temperature or set temperature of the thermally responsive material but below the decomposition temperature of the active ingredient. The starting material is then cooled and solidified in the molding chamber into a desired shaped form (i.e. the shape of the mold). The starting material, when at a temperature that is greater than its glass transition temperature or its set temperature, is sufficiently flowable to be easily injected or pumped into the molding chamber.

As used herein, "thermally responsive material" shall include materials that, as the temperature applied to the material is increased, become softer, and as the temperature applied is reduced, the materials conversely becomes harder and have reduced flow. In the case of gels, "set temperature" shall mean the temperature at which a gel-forming material rapidly solidifies through the gelation process.

In another embodiment, the first portion or core may be prepared by thermal cycle injection molding using the method and apparatus, in which the mold is cycled between at least two temperatures, as described in United States Patent Application Publication No. 20030086973. In this embodiment, the first portion or core may be formed by injecting a starting material in flowable form into a heated molding chamber. The starting material may comprise an active ingredient and a thermoplastic material at a temperature above the glass transition temperature or set temperature of the thermally responsive material but below the decomposition temperature of the active ingredient. The starting material is then cooled and solidified in the molding chamber into a desired shaped form (i.e. the shape of the mold).

According to either of these molding methods, the starting material must be in flowable form. For example, it may comprise solid particles suspended in a molten matrix such as a polymer matrix. Alternatively, the starting material may be completely molten or in the form of a paste. In one embodiment, the starting material may comprise an active ingredient dissolved in a molten material. Alternatively, the starting material may be made by dissolving a solid in a solvent, which solvent may then be evaporated from the starting material after it has been molded.

The starting material may comprise any edible material which is desirable to incorporate into a shaped form, including active ingredients such as those active ingredients previously described with respect to the core, nutritionals, vitamins, minerals, flavors, sweeteners, and the like. Typically, the starting material comprises an active ingredient and a thermally responsive material. The thermally responsive material may be any edible material that is flowable at a temperature between about 37° C. and about 250° C., and that is a solid or semi-solid at a temperature between about −10° C. and about 35° C. When it is in the fluid or flowable state, the flowable starting material may comprise a dissolved or molten component, and optionally a solvent such as for example water or organic solvents, or combinations thereof. The solvent may be partially or substantially removed by drying.

Suitable flowable, starting materials include, but are not limited to those thermally responsive materials such as film forming polymers, gelling polymers, hydrocolloids, low melting hydrophobic materials such as fats and waxes, non-crystallizable carbohydrates, and the like.

Examples of suitable thermally responsive materials include, but are not limited to water-soluble polymers such as polyalkylene glycols, polyethylene oxides and derivatives, and sucrose-fatty acid esters; fats such as cocoa butter, hydrogenated vegetable oil such as palm kernel oil, cottonseed oil, sunflower oil, and soybean oil; free fatty acids and their salts; mono- di- and triglycerides, phospholipids, waxes such as carnuba wax, spermaceti wax, beeswax, candelilla wax, shellac wax, microcrystalline wax, and paraffin wax; fat-containing mixtures such as chocolate; sugar in the form of an amorphous glass such as that used to make hard candy forms, sugar in a supersaturated solution such as that used to make fondant forms; carbohydrates such as sugar-alcohols (for example, sorbitol, maltitol, mannitol, xylitol and erythritol), or thermoplastic starch; and low-moisture polymer solutions such as mixtures of gelatin and other hydrocolloids at water contents up to about 30%, such as for example those used to make "gummi" confection forms. In one embodiment, the thermally responsive material is a blend of fats and mono- and diglycerides.

In one embodiment of the invention, the flowable materials may comprise a film former such as a cellulose ether, e.g. hydroxypropylmethylcellulose or a modified starch, e.g. waxy maize starch; optionally a polycarbohydrate, e.g. maltodextrin; optionally a hydrocolloid, e.g. xanthan gum or carrageenan, or a sugar, e.g. sucrose; and optionally a plasticizer such as polyethylene glycol, propylene glycol, vegetable oils such as castor oil, glycerin, and mixtures thereof.

Any film former known in the art is also suitable for use as a thermally responsive material. Examples of suitable film formers include, but are not limited to, polyvinylalcohol (PVA), polyvinylpyrrolidone (PVP), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethyl cellulose (HEMPMC), methacrylic acid and methacrylate ester copolymers, polyethylene oxide and polyvinylpyrrolidone copolymers, gelatin, proteins such as whey protein, coaggulatable proteins such as albumin, casein, and casein isolates, soy protein and soy protein isolates, pre-gelatinized starches, and polymers and derivatives and mixtures thereof.

One suitable hydroxypropylmethylcellulose compound is HPMC 2910, which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename, "METHOCEL E." METHOCEL E5, which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, METHOCEL E6, which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20° C. in a 2% aqueous solution as determined by a Ubbelohde viscometer.

As used herein, "degree of substitution" shall mean the average number of substituent groups attached to a anhydroglucose ring, and "hydroxypropyl molar substitution" shall mean the number of moles of hydroxypropyl per mole anhydroglucose.

As used herein, "modified starches" include starches that have been modified by crosslinking, chemically modified for improved stability, or physically modified for improved solubility properties. As used herein, "pre-gelatinized starches" or "instantized starches" refers to modified starches that have been pre-wetted, then dried to enhance their cold-water solubility. Suitable modified starches are commercially available from several suppliers such as, for example, A.E. Staley Manufacturing Company, and National Starch & Chemical Company. One suitable modified starch includes the pre-gelatinized waxy maize derivative starches that are commercially available from National Starch & Chemical Company under the tradenames, "PURITY GUM" and "FILMSET," and derivatives, copolymers, and mixtures thereof. Such waxy maize starches typically contain, based upon the total weight of the starch, from about 0 percent to about 18 percent of amylose and from about 100% to about 88% of amylopectin.

Suitable tapioca dextrins include those available from National Starch & Chemical Company under the tradenames "CRYSTAL GUM" or "K-4484," and derivatives thereof such as modified food starch derived from tapioca, which is available from National Starch and Chemical under the tradename, "PURITY GUM 40," and copolymers and mixtures thereof.

Examples of suitable hydrocolloids (also referred to herein as gelling polymers) include but are not limited to alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, chitosan, and derivatives and mixtures thereof.

Suitable xanthan gums include those available from C. P. Kelco Company under the tradenames, "KELTROL 1000," "XANTROL 180," or "K9B310."

Thermoplastic materials that can be molded and shaped when heated are suitable for use as the thermally responsive material, and include both water soluble and water insoluble polymers that are generally linear, not crosslinked, nor strongly hydrogen bonded to adjacent polymer chains. Examples of suitable thermoplastic materials include: chemically modified cellulose derivatives such as hydroxypropyl cellulose (HPC), hydroxypropylmethyl cellulose (HPMC), methyl cellulose (MC), cellulose acetate (CA), ethyl cellulose (EC), cellulose acetate butyrate (CAB), cellulose propionate; vinyl polymers such as polyvinyl alcohol (PVA) and polyvinyl pyrrolidone (PVP); thermoplastic starch; thermoplastic gelatin, natural and chemically modified proteins such as gelatin, soy protein isolates, whey protein, myofibrillar proteins, and the milk derived caseinate proteins; and derivatives and combinations thereof.

Any plasticizer known in the pharmaceutical art is suitable for use in the flowable material, and may include, but not be limited to polyethylene glycol; glycerin; sorbitol; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof. In solutions containing a cellulose ether film former, an optional plasticizer may be present in an amount, based upon the total weight of the solution, from about 0% to about 40%.

Any thickener known in the art may optionally be added to the thermally responsive material. Additional suitable thickeners include, but are not limited to, cyclodextrin, crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are suitable and are exemplified by xylitol and erythritol, respectively.

The flowable material may optionally comprise adjuvants or excipients, which may comprise up to about 20% by weight of the flowable material. Examples of suitable adjuvants or excipients include detackifiers, humectants, surfactants, anti-foaming agents, colorants, flavorants, sweeteners, opacifiers, and the like. In one embodiment, the flowable material comprises less than 5% humectants, or alternately is substantially free of humectants, such as glycerin, sorbitol, maltitol, xylitol, or propylene glycol. Humectants have traditionally been included in pre-formed films employed in enrobing processes, such as that disclosed in U.S. Pat. Nos. 5,146,730 and 5,459,983 to ensure adequate flexibility or plasticity and bondability of the film during processing. Humectants function by binding water and retaining it in the film. Pre-formed films used in enrobing processes can typically comprise up to 45% water. Disadvantageously, the presence of humectant prolongs the drying process, and can adversely affect the stability of the finished dosage form.

In another embodiment, the core may be a hollow or evacuated core. For example, the core may be an empty capsule shell. Alternatively, a hollow core may be prepared for example by injection molding or shell molding. In one such method, flowable material is injected into a mold cavity, the cavity is brought to a temperature at which the outer surface of the core (which is in contact with the mold) begins to solidify or set. The excess flowable material from the center of the core is then withdrawn from the mold using suitable means, for example a piston pump. In another such method, an empty capsule is used as a sub-core, and a coating layer is formed thereon by methods known in the art such as, for example, spray-coating, dip-coating, injection cycle molding as described in, for example, United States Patent Application Publication No. 20030086973. In certain embodiments of the invention, the core may further comprise any of the aforementioned subcoatings applied by any method known in the art, for example spraying, compression, or molding. In certain other embodiments of the invention, the core may be substantially free of a subcoating.

In another embodiment of the invention, the core contains at least in part one or more inserts. The inserts can be made in any shape or size. For instance, irregularly shaped inserts can be made, that is shapes having no more than one axis of symmetry. Cylindrically shaped inserts may also be made. The insert may be made using conventional techniques such as panning, compression, or molding. In one embodiment, the insert is prepared using the injection molding methods and apparatus as described herein.

In one embodiment of the invention, the insert may have an average diameter from about 100 to about 1000 microns. In another embodiment of this invention, the insert may have an average diameter or thickness from about 10% to about 90% of the diameter or thickness of the core. In yet another embodiment of this invention, the core may comprise a plurality of inserts.

In another embodiment, the insert may have an average diameter, length, or thickness greater than about 90% of the diameter or thickness of the core, for example the insert may have an average length greater than about 100% of the thickness of the core.

In another embodiment of the invention, the core, the insert (if employed), the inlaid portion or any combination thereof may comprise a microelectronic device (e.g. an electronic "chip") which may be used as an active component or to control, for example, the rate of release of active ingredients within the core or insert in response to an input signal. Examples of such microelectronic devices are as follows:

(1) Integrated, self-regulating responsive therapeutic devices including biosensors, electronic feedback and drug/countermeasure release devices which are fully integrated. Such devices eliminate the need for telemetry and human intervention, and are disclosed, for example, at www.chiprx.com/products.html, which is incorporated herein by reference;

(2) Miniaturized diagnostic imaging systems which comprise a swallowable capsule containing a video camera, and are disclosed, for example, at www.givenimaging.com/usa/default.asp, which is incorporated herein by reference;

(3) Subcutaneous glucose monitors which comprise implantable or insertable sensor devices which detect changes in glucose concentration within intestinal fluid, and communicate to an external detector and data storage device. Such devices are disclosed, for example, at www.applied-medical.co.uk/glucose.htm, which is incorporated herein by reference;

(4) Microdisplay vision aid devices encapsulated in an artificial intraocular lens. Such devices include a receiver for power supply, data and clock recovery, and a miniature LED array flip-chip bonded to a silicon CMOS driver circuit and micro optics, and are disclosed, for example, at http://ios.oe.uni-duisberg.de/e/, which is incorporated herein by reference. The microdisplay device receives a bit-stream+energy wireless signal from a high dynamic range CMOS camera placed outside the eye which generates a digital black & white picture which is converted by a digital signal processing unit (DAP) into a serial bit-stream with a data rate of approximately 1 Mbit/s. The image is projected onto the retina;

(5) Microchips used to stimulate damaged retinal cells, allowing them to send visual signals to the brain for patients with macular degeneration or other retinal disorders. The chip is 2 mm×25 microns, and contains approximately 5,000 microscopic solar cells ("microphotodiodes"), each with its own stimulating electrode. These microphotodiodes convert the light energy from images into electrical chemical impulses that stimulate the remaining functional cells of the retina in patients with AMD and RP. Such microchips are disclosed, for example, at www.optobionics.com/artificial-retina.htm, which is incorporated herein by reference;

(6) Disposable "smart needles" for breast biopsies which display results in real time. The device fits into a 20 to 21 gauge disposable needle that is connected to a computer, as the needle is inserted into the suspicious lesion. The device measures oxygen partial pressure, electrical impedance, temperature, and light scattering and absorption properties including deoxygenated hemoglobin, vascularization, and tissue density. Because of the accuracy benefits from the six simultaneous measurements, and real-time nature of the device, it is expected to exceed the accuracy levels achieved by the core needle biopsy procedure and approach the high level of accuracy associated with surgical biopsies. Further, if cancer is found, the device can be configured to deliver various therapies such as cancer markers, laser heat, cryogenics, drugs, and radioactive seeds. Such devices are disclosed, for example, at www.bioluminate.com/description.html, which is incorporated herein by reference; and (7) Personal UV-B recorders, which are instrument grade devices for measuring and recording UVB exposure and fit into a wrist-watch face. They may also be worn as a patch.

In one embodiment of the invention, only the core comprises one or more active ingredients. In another embodiment of this invention, only the inlaid portion comprises one or more active ingredients. In yet another embodiment of this invention, only the insert comprises one or more active ingredients. In yet another embodiment of this invention, both the core and inlaid portion comprise one or more active ingredients. In yet another embodiment of this invention, one or more of the core, the inlaid portion, or the insert comprises one or more of the active ingredients. Optionally, any of the coatings may further comprise one or more active ingredients.

The shell and/or inlaid portion may be made from the aforementioned thermally responsive materials, which for food and pharmaceutical uses may be any material that has been approved for use in foods and pharmaceuticals and can be molded, including for example, film formers, low-melting hydrophobic materials, gelling polymers, thickeners, plasticizers, adjuvants, and excipients.

In one embodiment, the inlaid portion comprises at least about 50%, e.g. at least about 80%, or at least about 90% of a material selected from film formers, gelling polymers, low-melting hydrophobic materials, non-crystallizable sugars or sugar alcohols, and mixtures thereof. In another embodiment, the inlaid portion comprises at least about 50%, e.g. at least about 80% or at least about 90% of a material selected from film formers, gelling polymers, low-melting hydrophobic materials, and mixtures thereof.

In one embodiment of the invention, the flowable material comprises gelatin as a gelling polymer. Gelatin is a natural, thermogelling polymer. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In one embodiment, the flowable material is an aqueous solution comprising 20% 275 Bloom pork skin gelatin, 20% 250 Bloom Bone Gelatin, and approximately 60% water.

In another embodiment of the invention, the inlaid portion of the dosage form comprises at least about 80%, e.g. at least about 90%, of a material selected from film formers, gelling polymers (hydrocolloids), thermoplastic materials, low-melting hydrophobic materials, non-crystallizable sugars, and mixtures thereof.

The inlaid portion of the dosage form may be molded into the cavity of the dosage form via any molding means known in the art. In one embodiment of the invention, the inlaid portion is applied to the dosage form using thermal setting injection molding or thermal cycle injection molding as described above.

Figure 4A:
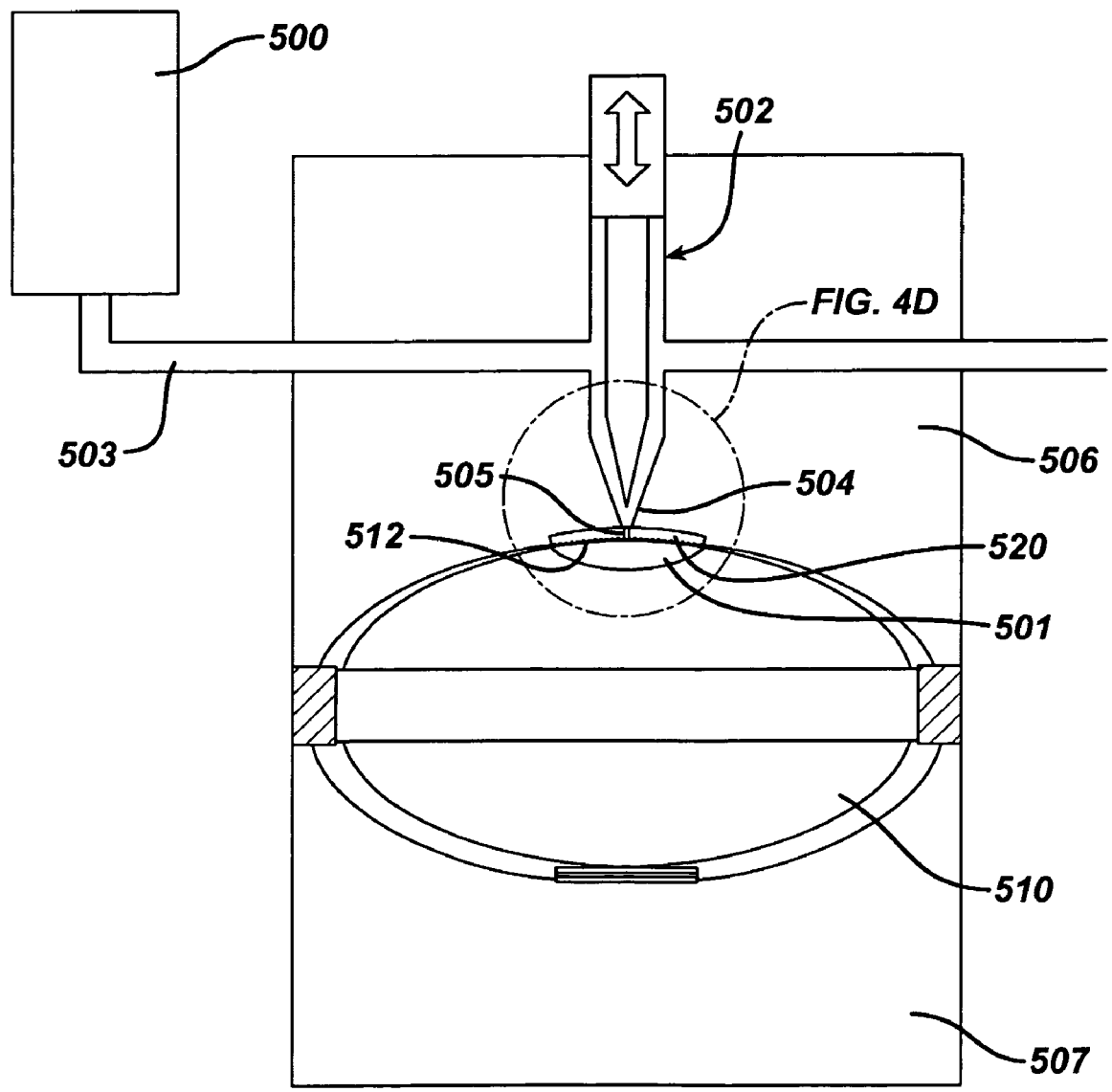
FIGS. 4A-C are simplified cross-sectional views of an injection molding module apparatus according to the invention, which provides for the application of a flowable material to the cavities of dosage forms.
Figure 4B:
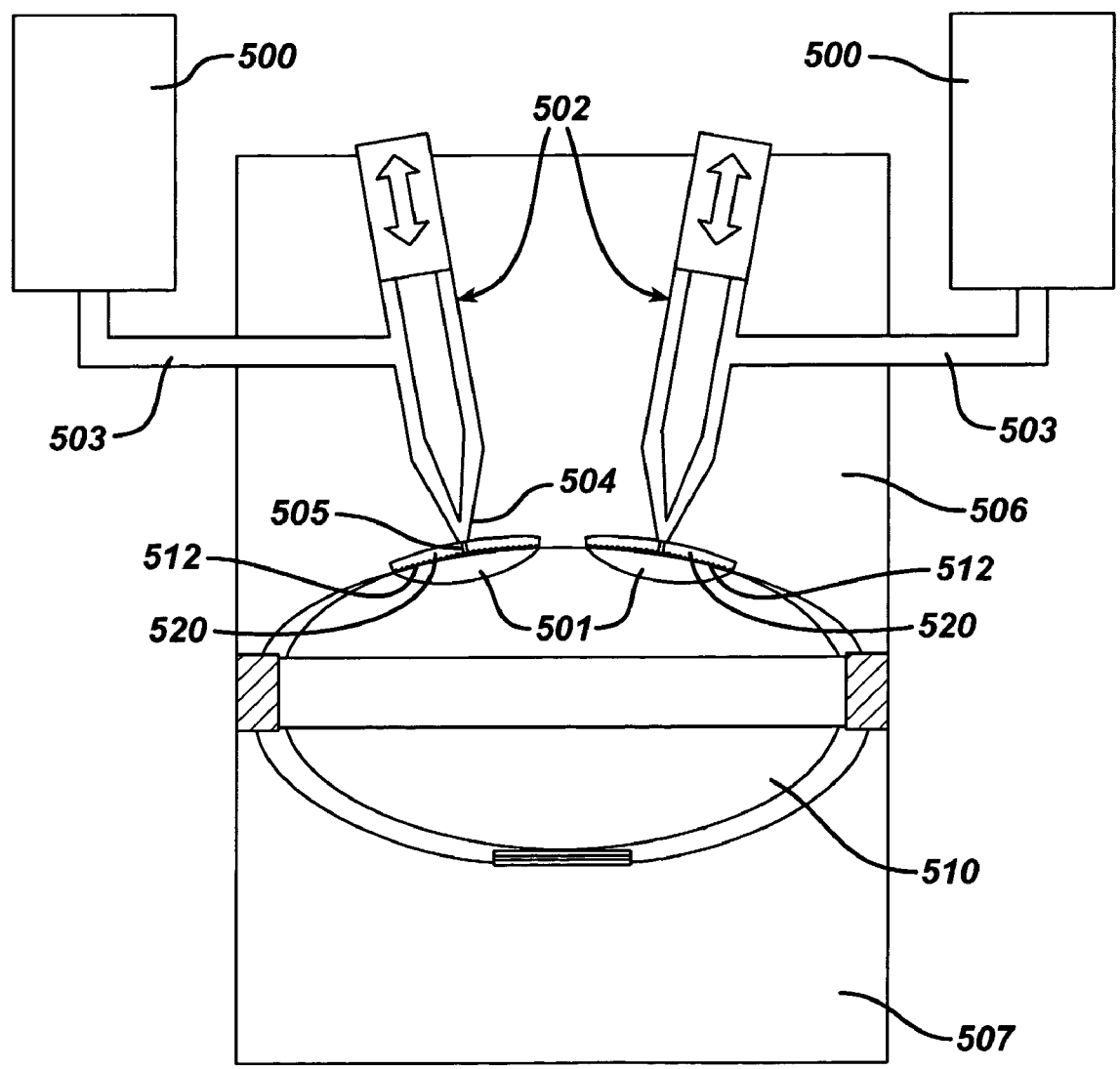
Figure 4C:
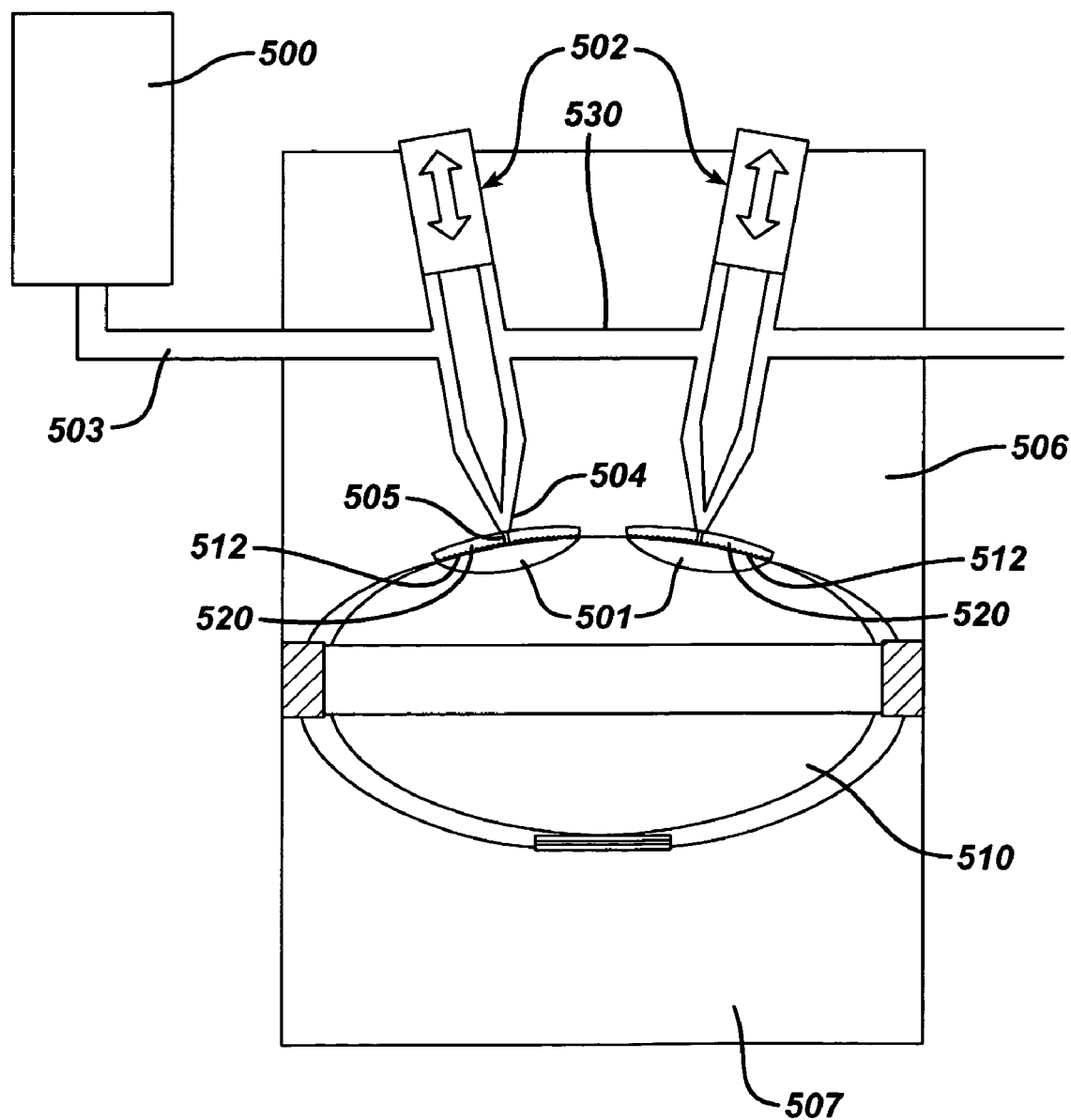

As shown in FIG. 4A and FIG. 4B, the flowable material for insertion into the cavities may be kept in one or more reservoirs 500 until the desired time for filling the cavities 501 of the core or the shell of the dosage form 510. The flowable material may then be transported from the reservoirs 500 to the desired location in the cavities 501 via one or more feedlines 503 connected to one or more injector ports 502. FIG. 4B illustrates an embodiment wherein a multiple of reservoirs 500, feedlines 502, and injector ports 502 are used to fill multiple, discontinuous cavities 501 in the dosage form 510. FIG. 4C illustrates another embodiment wherein a single feedline 502 is branched in a manifold configuration 530 in order to permit the flowable material to feed into multiple injector ports 502. Although not shown, it may be possible to fill such multiple cavities 501 in the dosage form through one of many other ways such as, for example, having concentric feedlines and/or concentric nozzle tips. One skilled in the art would readily appreciate that a method suitable for filling such multiple cavities depending upon, for example, the location of the cavities on the dosage form and the difference, if any, in the type of flowable material required for each respective cavity.

Figure 4D:
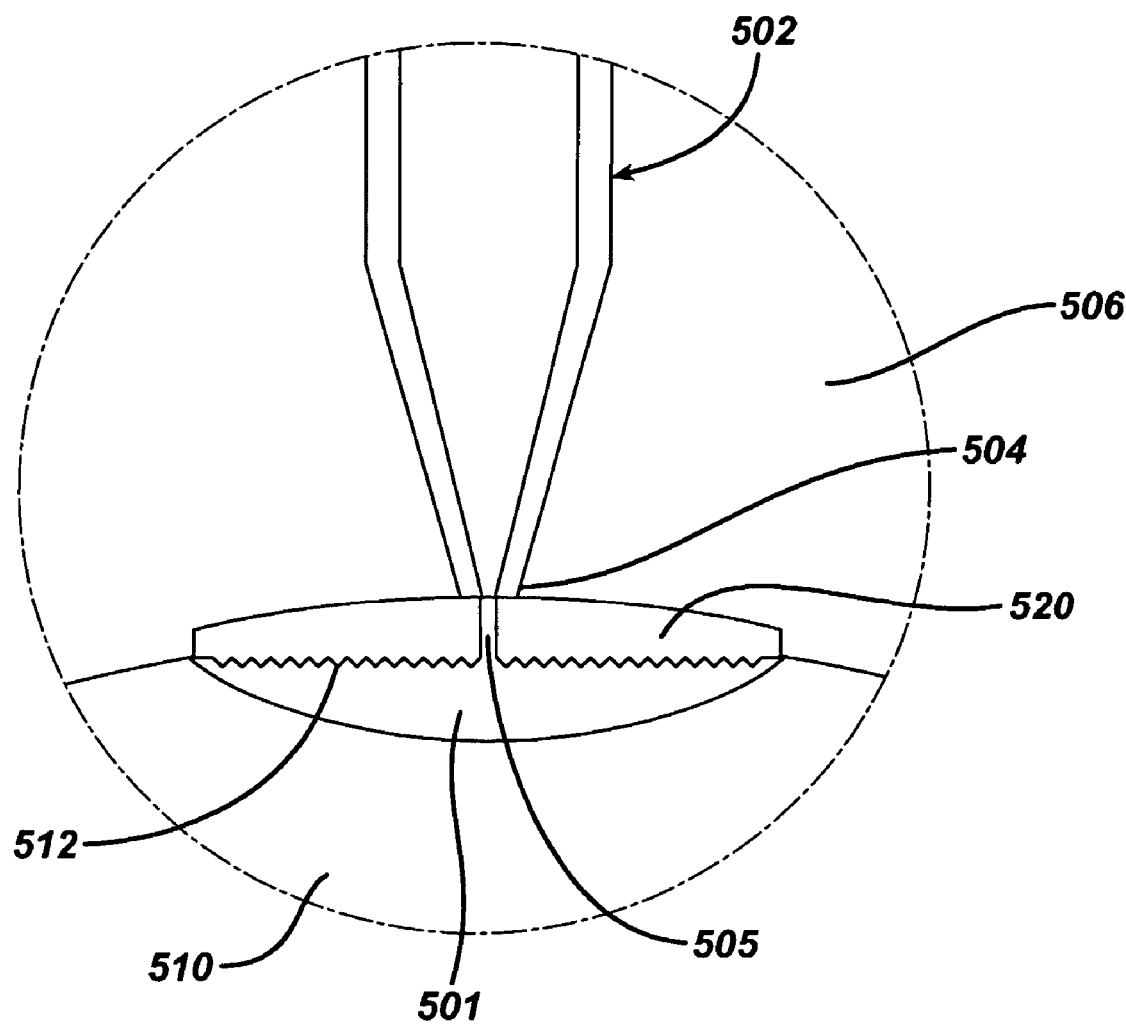
FIG. 4D is an enlarged, cross-sectional view of the injector port/cavity interface of the injection molding apparatus of FIG. 4A.

As shown in greater detail in FIG. 4D, a tip or valve 504 located at the bottom of each injector port 502 passes through a hole 505 in the surface of the upper mold 506 that is in alignment with the respective cavity 501 therebelow. The desired amount of flowable material passes through the tip or valve 504 and into the cavity 501. The valve 504 is then closed, which thus closes the hole 505 during the molding period. The location of the hole 505 is not critical, so long as it permits the flowable material to be injected into the appropriate cavity 501 of the dosage form 510. See also FIGS. 52, 53, and 54 of WO03/028990.

The upper mold 506 is engaged with either a holder or "collet" for the dosage form or a lower mold 507. Although the upper mold 506 and the lower mold 507 are illustrated as moving in a longitudinal manner in order to produce the molded dosage form, the operational direction of these pieces is not critical so long as the microrelief on the interior surface 506A of at least the upper surface is in alignment with the filled-in cavity portion 501 of the dosage form.

In embodiments when the cavity is filled with gelatin, and the gelatin portion contains a microrelief, the gelatin generally shrinks vertically, e.g., by about 50% to about 75% and laterally, e.g., by about 1% to about 10%. In order to compensate for this shrinkage, the diffractive relief pattern molded into the wet gelatin is sized to be about 50% to about 75% larger in the vertical dimension and about 1% to about 10% larger in the horizontal dimension than the dimensions of the pattern in the final dried dosage form product. Therefore, for example, if the final product has a diffractive grating of about 500 lines or grooves per millimeter, the diffractive pattern etched into the surface of the mold would be a negative pattern and have about 476 lines or grooves per millimeter. Likewise in the vertical dimension, if the linear ridges making up the diffractive grating of the final, dried dosage form product are about ⅔ microns in height, then the diffractive pattern etched into the surface of the mold would be a negative pattern and have about 3 times the vertical dimension of the grating in the dried, finished product or approximately 2 microns.

Figure 5A:
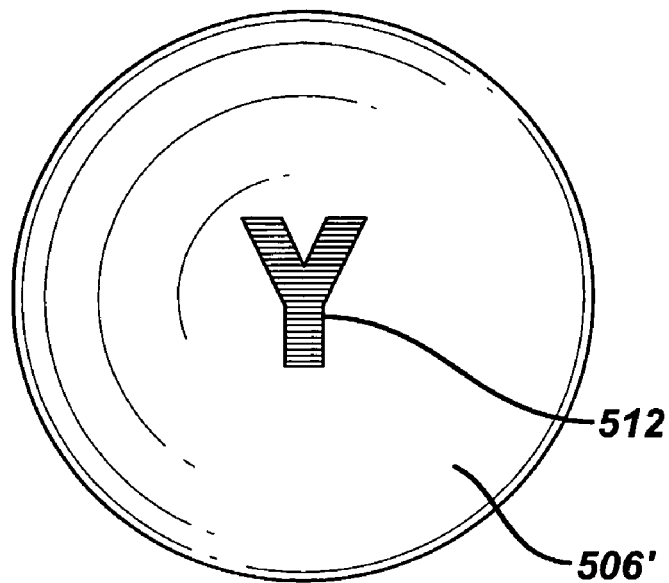
FIG. 5A depicts a plan view of a mold surface showing an exemplary microrelief pattern for use in an injection molding module according to the present invention.
Figure 5B:
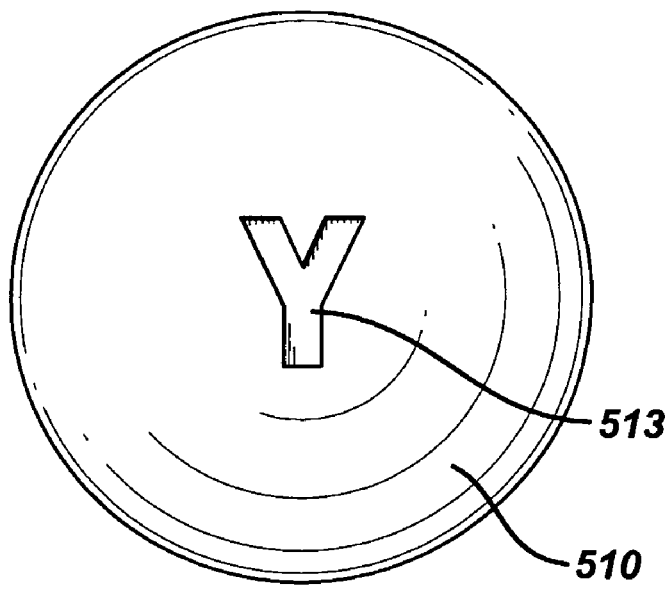
FIG. 5B illustrates a plan view of an exemplary dosage form containing a "Y-shaped" cavity.

FIG. 5A shows an example of the plan view of the internal surface 506A of the upper mold 506, wherein a microrelief 512, with ridges and grooves arranged in an exemplary shape, e.g. an overall "Y" shape, is engraved into the internal surface 506'. In this example, the overall shape of the microrelief 512 may either correspond with the overall "Y-shaped" cavity 513 as illustrated in FIG. 5B or may extend beyond the perimeter of the actual cavity (not shown). Methods for etching the internal surface 506', such as by use of a laser, mechanical scribing, or acid etching, in order to obtain the desired microrelief pattern in the desired location are well known in the art and disclosed in, for example, pages 17-18 of WO 03/005839, U.S. Pat. No. 6,410,213 B1, and the publication, Photonics Spectra (June 2004).

Figure 6A:
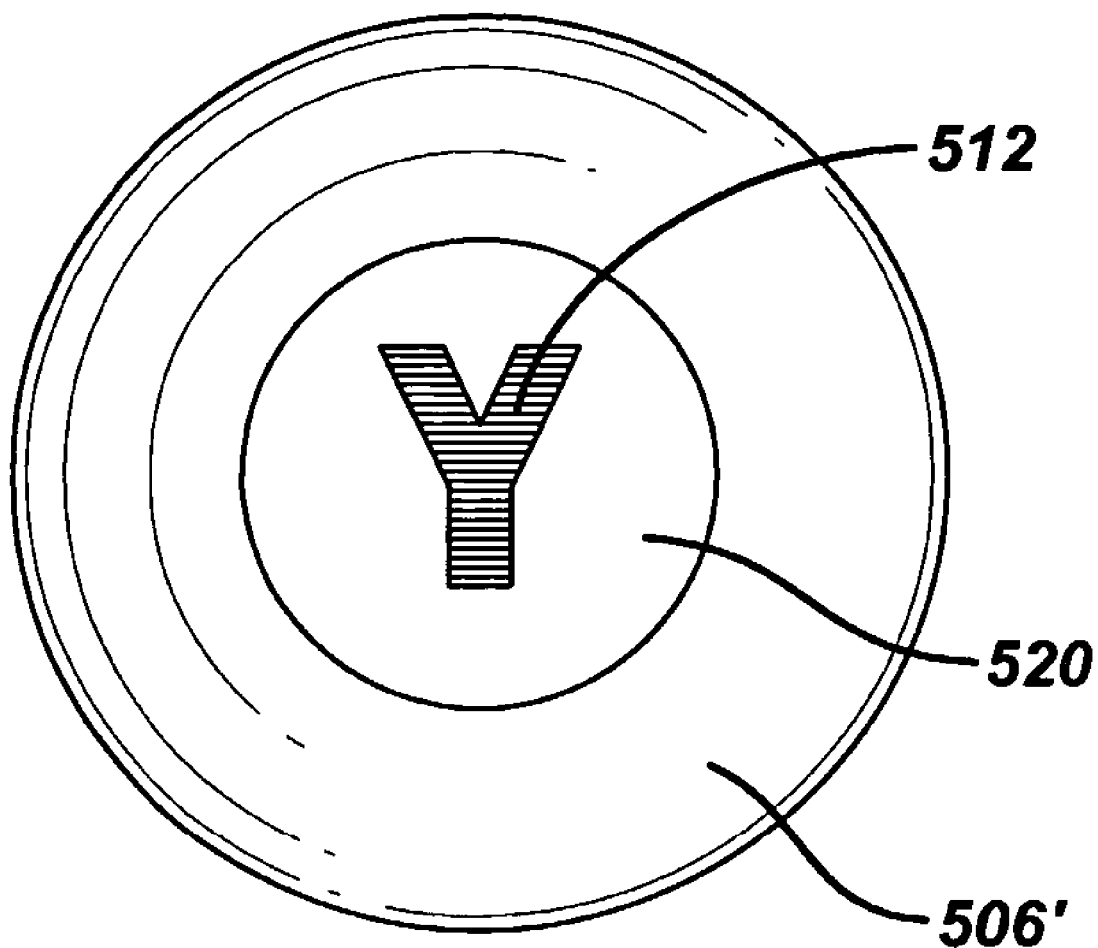
FIG. 6A depicts a plan view of a mold surface showing one type of removable changepart having a surface with an exemplary microrelief pattern.
Figure 6B:
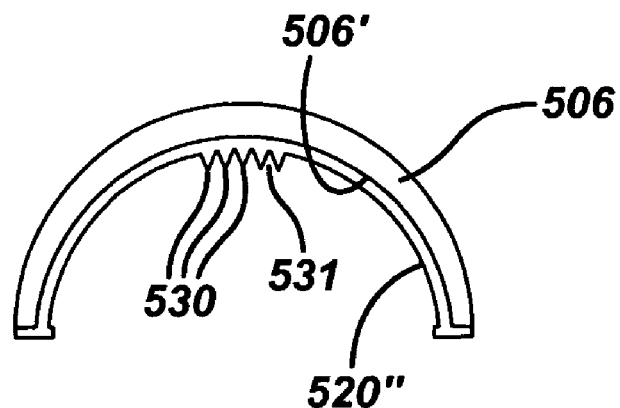
FIGS. 6B-6D illustrate cross sectional views of alternative removable changeparts, each having a surface with an exemplary microrelief pattern for use in the present invention.
Figure 6C:
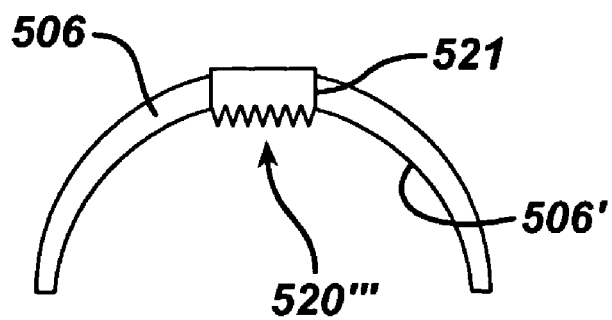
Figure 6D:
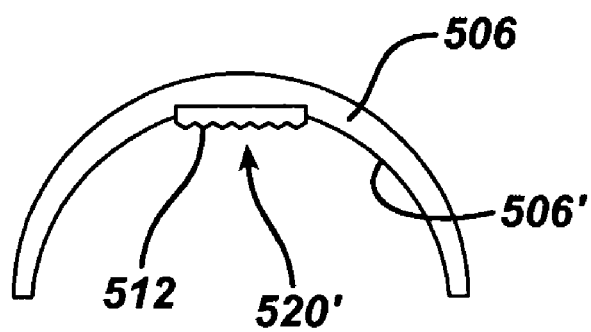

In an alternative embodiment shown in FIGS. 6A and 6D, a removable change-part 520,520' such as a thin film or foil, containing the desired microrelief 512 may be inserted on to the internal surface 506' of the upper mold, or in the internal surface of one of the dies used in a tablet press, via any known means for removably attaching the change-part such as, for example adhesives. In alternative embodiment shown in FIG. 6B and FIG. 6C, respectively, the removable change-part 520 may extend across the entire internal surface 506' of the upper mold 506 (see changepart 520" in FIG. 6B), or may be friction-fit into an opening in the upper mold 506 (see changepart 520'" in FIG. 6C). Advantageously, the changepart 520 used in this embodiment could easily be removed and replaced with another changepart having an alternative microrelief pattern with minimal cost and production cycle time loss.

Suitable changepart materials include any substance that is capable of holding a microrelief image, such as aluminum, tin, gold, silver, nickel, copper, and their alloys, plastics that are solid at temperature greater than 250° C., and mixtures thereof. The size and thickness of the changepart may vary depending upon, for example, the surface area of dosage form and the desired microrelief pattern, but will generally have a thickness of from about 10 microns to about 5000 microns and a surface area of from about greater than 0% to less than about 100% of the dosage form face, e.g., greater than about 10% and less than about 90% or greater than about 25% and less than about 50%. "Face," as used herein, is the portion of a compressed tablet formed by the upper and lower punch faces, and includes one-half of the overlap area of a rim as illustrated in United States Patent Application Publication No. 20040109889.

In an alternative embodiment, the microrelief may be stamped into the molded inlaid portion 501 of the dosage form using conventional stamping means containing the desired microrelief pattern. These stamping means are well known in the art and disclosed in, for example, WO 01/10464, Begleiter, *Edible Holography: The Application of Holographic Techniques to Food Processing,"* 1461 SPIE Practical Holography V 102-109 (1991); WO 01/10464; and WO 03/00589.

In embodiments where the inlaid portion is formed by injection molding, the need for direct-compression filler-binders such as microcrystalline cellulose, spray-dried lactose, mineral salts such as calcium phosphate, crystalline sugars such as sucrose, dextrates and the like, may be minimized or eliminated. Other known dosage forms, such as those produced via the inclusion of compression-coated shells, typically comprise at least about 30% of such direct-compression filler-binders. See, e.g., WO 00/18447. Disadvantageously, the inclusion of these materials would otherwise disadvantageously detract from the clarity and stability of the inlaid portion. Advantageously in this embodiment, the inlaid portion of the present invention may comprise less than about 10%, e.g. less than about 1% or less than about 0.1%, of such direct-compression filler-binders.

In one embodiment wherein the cavity passes directly through the dosage form (not shown), the cavity may be filled with flowable material, then the microrelief may be applied to either the top surface and/or the bottom surface of the filled-in portion via any means known in the art. In this embodiment, the microrelief may be applied to one surface via injection molding or stamping as set forth herein. Alternatively, in embodiments wherein it is desired to apply a microrelief to both the top surface and the bottom surface, the bottom dosage form collet may be replaced with a mold cavity having a microreliefed interior surface.

After the mold is filled with the desired amount of flowable material, the closed mold may then be adjusted to an appropriate temperature and for a time sufficient to set the flowable material within the cavity 501 of the dosage form. Although these parameters may vary depending upon, for example, the type and amount of flowable material, typically the molding temperature is from about 50° C. to about 120° C. and the molding time is from about 1 seconds to about 10 seconds.

In one embodiment, the inlaid portion may be substantially free of pores having a diameter of about 0.5 microns to about 5 microns. As used herein, "substantially free" means that the inlaid portion has a pore volume of less than about 0.02 cc/g, e.g. less than about 0.01 cc/g or less than about 0.005 cc/g, in the pore diameter range of about 0.5 microns to about 5 microns. Typical compressed materials have pore volumes of more than about 0.02 cc/g in this pore diameter range. Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d=-(4\gamma(\cos\theta))/P$ where $\gamma$ is the surface tension of liquid mercury, $\theta$ is the contact angle between mercury and the sample surface and P is the applied pressure.

Equipment used for pore volume measurements:
1. Quantachrome Instruments PoreMaster 60.
2. Analytical Balance capable of weighing to 0.0001 g.
3. Desiccator.

Reagents used for measurements:
1. High purity nitrogen.
2. Triply distilled mercury.
3. High pressure fluid (Dila AX, available from Shell Chemical Co.).
4. Liquid nitrogen (for Hg vapor cold trap).
5. Isopropanol or methanol for cleaning sample cells.
6. Liquid detergent for cell cleaning.

Procedure:

The samples remain in sealed packages or as received in the dessicator until analysis. The vacuum pump is switched on, the mercury vapor cold trap is filled with liquid nitrogen, the compressed gas supply is regulated at 55 psi., and the instrument is turned on and allowed a warm up time of at least 30 minutes. The empty penetrometer cell is assembled as described in the instrument manual and its weight is recorded. The cell is installed in the low pressure station and "evacuation and fill only" is selected from the analysis menu, and the following settings are employed:

Fine Evacuation time: 1 min.
Fine Evacuation rate: 10
Coarse Evacuation time: 5 min.

The cell (filled with mercury) is then removed and weighed. The cell is then emptied into the mercury reservoir, and two tablets from each sample are placed in the cell and the cell is reassembled. The weight of the cell and sample are then recorded. The cell is then installed in the low-pressure station, the low-pressure option is selected from the menu, and the following parameters are set:

Mode: Low pressure
Fine evacuation rate: 10
Fine evacuation until: 200 µHg
Coarse evacuation time: 10 min.
Fill pressure: Contact +0.1
Maximum pressure: 50
Direction: Intrusion And Extrusion
Repeat: 0
Mercury contact angle; 140
Mercury surface tension: 480

Data acquisition is then begun. The pressure vs. cumulative volume-intruded plot is displayed on the screen. After low-pressure analysis is complete, the cell is removed from the low-pressure station and reweighed. The space above the mercury is filled with hydraulic oil, and the cell is assembled and installed in the high-pressure cavity. The following settings are used:

Mode: Fixed rate
Motor speed: 5
Start pressure: 20
End pressure: 60,000
Direction: Intrusion and extrusion
Repeat: 0
Oil fill length: 5
Mercury contact angle: 140
Mercury surface tension: 480

Data acquisition is then begun and graphic plot pressure vs. intruded volume is displayed on the screen. After the high pressure run is complete, the low-and high-pressure data files of the same sample are merged.

In one embodiment, the dosage form contains a core having two faces and a belly band therebetween, and a shell having a thickness from about 100 microns to about 400 microns that substantially covers the one face surface. The other face surface is compositionally different from the shell. The shell, which may contain, based upon the total weight of said shell, less than about 50 percent crystallizable sugar, bears a microrelief.

Figure 7A:
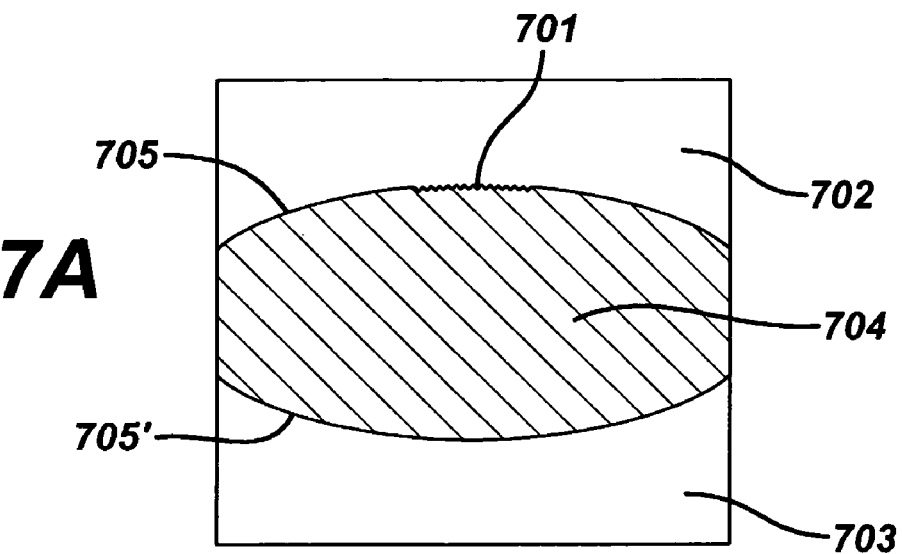
FIG. 7A is a simplified cross-sectional illustration of a molding apparatus module for a compressed powder dosage form.

Another embodiment of the present invention is directed to a dosage form wherein the core is comprised of a powder blend containing a plastically deforming compressible material. In this embodiment as illustrated in FIG. 7, the core 704 may be formed by first adding the powder blend into the desired mold arrangement, such as one with an upper punch 702 and a lower punch 703. At least one internal surface 705, 705' of the molding arrangement contains at least one micrograph 701 with a positive image engraved into its internal surface, such as that illustrated in FIG. 5A. These punches may be used in any conventional compression tablet press (not shown) having an upper punch and a lower punch known in the art, wherein the interior surface of the upper and/or lower punch contains at least one micrograph.

As used herein, "plastically deforming compressible material" shall mean any excipient added to core materials, which during compression, flows and assumes the shape of the microrelief engraved in the punch face. Examples of suitable plastically deforming compressible materials include polyethylene glycol, fats, waxes, and mixtures thereof.

Figure 7B:
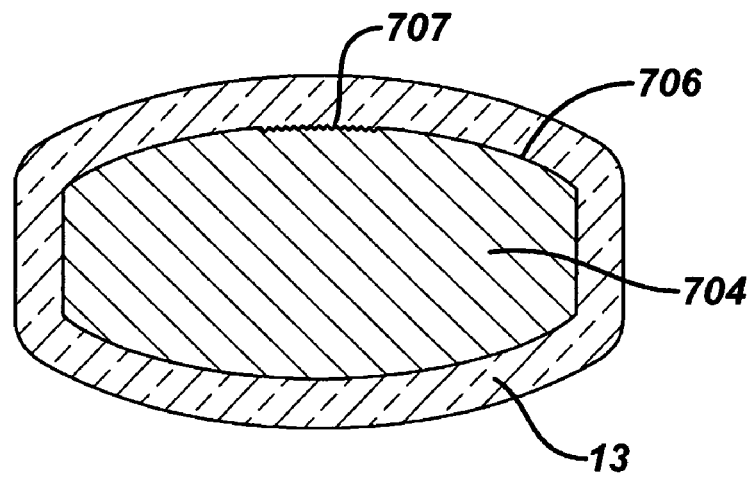
FIGS. 7B-7C depict a cross sectional view of the dosage forms containing an optional top coating resulting therefrom.

After the powder blend is compressed via a compression tablet press, a non-opaque, e.g., clear or semi-transparent, top coating 13 may then be applied to the surface 706 of the resulting core 704, which contains a micrograph 707 as illustrated in FIG. 7B, via any of the above-described coating application methods and at a temperature below the melting temperature of the plastically deforming compressible material. Typically, such temperature may range from about 5° C. to about 120° C. The top coating 13 should also be applied to the core 704 at the location of the micrograph 707. Examples of suitable top coating 13 materials include, but are not limited to aminoalkyl methacrylate copolymers, which are commercially available under the tradename, "Eudragit E," and polymethylmethacrylate. The coated dosage form may contain, based upon the total weight of the dosage form, from about 1 percent to about 10 percent of the top coating 13.

Figure 7C:
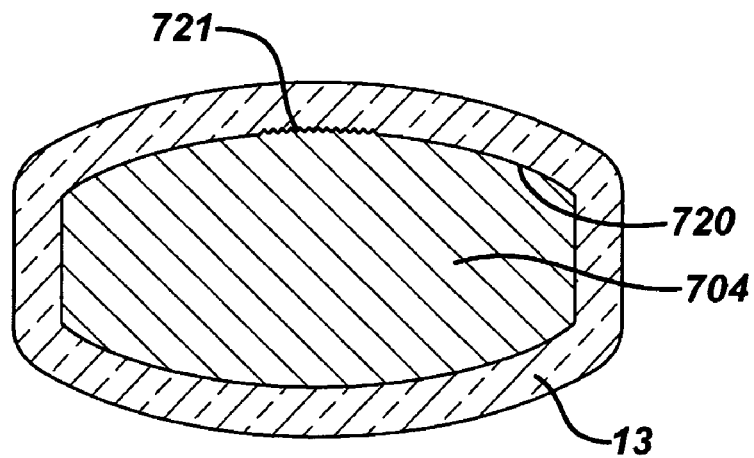

After the top coating 13 is set on the core 705 such that the internal surface 720 of the top coating 13 possesses a negative image 721 of the micrograph pattern 707 formed on the exterior surface 706 of the core 704, the coated dosage form may then optionally be heated to a temperature sufficient to melt at least the surface of the core 705. Although this temperature may vary depending upon, for example, the composition of the powder blend, typically the temperature may range from 20° C. to about 200° C. In this embodiment, the core material may optionally contain, based upon the total weight of the core, from about 10 to about 50, of an absorbent excipient having a porous structure such as dicalcium phosphate, tricalcium phosphate, calcium silicate, and mixtures thereof. The dosage form may then be cooled to ambient temperature. The resulting dosage form uniquely possesses a top coating 13 with an internal surface 720 containing at least one micrograph 721 in the internal surface of the top coating as illustrated in FIG. 7C.

Figure 9A:
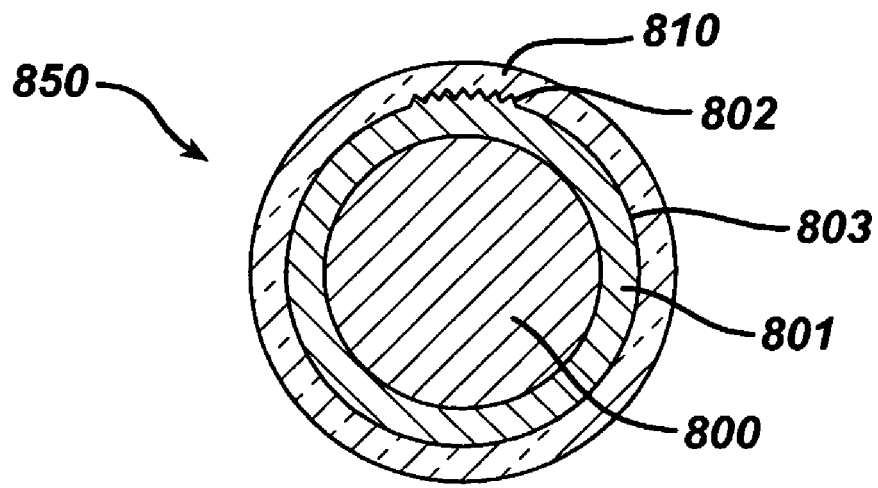
FIG. 9A depicts a cross-sectional view of another dosage form of this invention containing a core, a top coating, and a microreliefed- waxy layer therebeween.

In yet another embodiment as shown in FIG. 9A, a tablet core 800 comprised of a powder blend containing a plastically deforming compressible material may be produced via injection molding or compression as aforementioned, wherein the surface of the resulting core does not possess a micrograph.

Optionally, the tablet core 800 may also contain the aforementioned absorbent excipient. A waxy layer 801 may then be applied to the surface of the core either via pan coating or via any of the aforementioned molding methods. A micrograph 802 may then be applied to the outer surface 803 of the waxy layer 801 either by stamping the pan-coated waxy layer surface with the desired micrograph pattern or via injection molding the micrograph pattern into the waxy layer 801 with a mold portion having a patterned inner surface. The dosage form 850 of this embodiment may contain, based upon the total weight of the coated dosage form 850, from about 1 percent to about 10 percent of the waxy layer 801.

The waxy layer 801 may be comprised of any material that will retain the image of the micrograph, but have a lower melting temperature than the melting temperature of the adjacent top coat 810. Examples of suitable materials for the waxy layer 801 include, but are not limited to, aliphatic polyesters; ascorbyl palmitate; hydrogenated castor oil; cetosteryl alcohol; cetyl alcohol; cetyl esters; sterols such as cholesterol; ethyl glycol palmitostearate; mono and di-glycerides; saturated polyglycolized glycerides, paraffin, poloxamer, polyethylene glycol; polyethylene oxide; sorbitan esters, polyoxyethylene stearates; suppository bases; stearyl alcohol, stearic acid; hydrogenated vegetable oil; waxes such as yellow, white, carnauba, sterotex, anionic emulsifying, microcrystalline, nonionic emulsifying waxes; and mixtures thereof.

A top coat 810, which is not opaque, may then be applied to the surface 803 of the waxy layer 801 via any means known in the art such as, for example, spraying, molding, or dipping. Advantageously, the top coating 810 should either partially or fully reside on the micrographed portion 802 of the waxy layer 801, and be comprised of a material that is rigid or not flowable at a temperature less than about 100° C., e.g., less than about 70° C. Examples of suitable top coatings 810 include those set forth above such as, for example, a blend of acrylate and hydroxypropylmethyl cellulose. The dosage form of this embodiment 850 may contain, based upon the total weight of the dosage form, from about 1 percent to about 10 percent of the top coating.

Figure 9B:
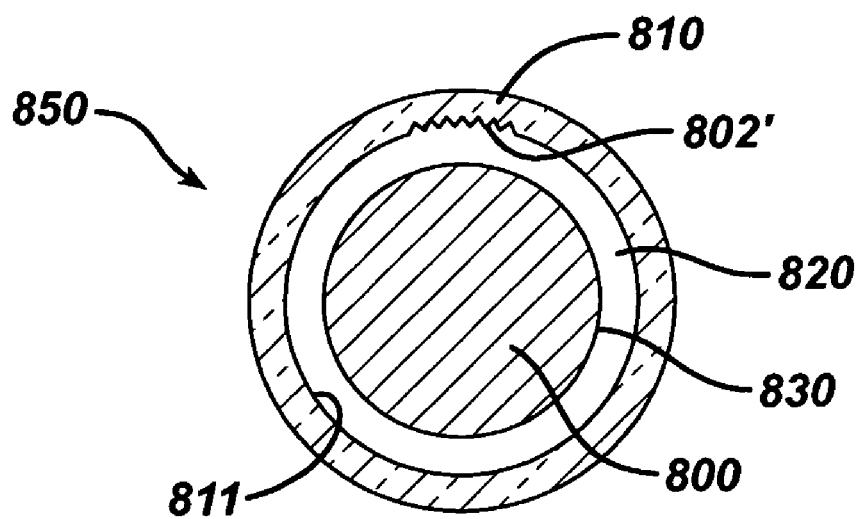
FIG. 9B depicts a cross-sectional view of the same dosage form after exposure to heat.

After the top coating 810 is dried, the resulting dosage form 850 may then be heated to a temperature in excess of the melting temperature of the waxy layer 801. In one embodiment, the temperature may also be less than the melting temperature of the core 800. As a result, the waxy layer 801 is substantially absorbed by the core 800, leaving the interior surface 811 of the top coating 810 with a negative image 802' of the microrelief 802, and the formation of an air gap 820 between the outer surface 830 of the core 800 and the inner surface 811 of the top coating 810 as illustrated in FIG. 9B.

The presence of the air gap creates an interface between the core 800 and the diffractive relief pattern 802' in the interior surface 811 of the top coating 810. The resulting change in the index of refraction through this interface causes a reflection of a portion of the incident light and thus a reconstruction of the holographic microrelief image 802' in the top coating 810. The portion of the light transmitted through the microrelief 802' also brightens the core surface 800 located in the background of the microrelief upon the light's reflecting from the core surface 800. See U.S. Pat. No. 4,921,319. In the embodiment wherein the core 800 also contains a printed image, this reflected light also permits the visualization of that printed image, with the result being a superimposition of a diffractive image over a printed image.

Advantageously, this embodiment is particularly suitable for providing a user with a visual quality control indication on the dosage form that would visibly change if the dosage form were exposed to adverse humidity or temperature conditions. For example, a micrograph pattern, such as the word, "EXPIRED," may be placed into the waxy layer of the dosage form. Then, so long as the waxy layer is made from a composition that melts at least at a temperature and or humidity that would also affect the efficacy of the pharmaceutical active ingredient, the micrograph pattern would not become visible to the user until the waxy layer was absorbed into the core.

Yet another embodiment of the present invention is directed to flakes or "glitter" comprised of film containing microreliefs that may be subsequently cut into smaller, desired shapes and sizes. Films suitable for use in this embodiment may be prepared from a polymeric mixture containing, based upon the total weight of the polymeric mixture, from about 5 percent to about thirty percent of a water insoluble, film forming polymer, and from about 70 percent to about 95 percent of an organic solvent.

Suitable water insoluble polymers include, but are not limited to cellulose acetate, ethylcellulose, and derivatives, copolymers and mixtures thereof. Suitable pH-dependent polymers include, but are not limited to methyl acrylate copolymers, such as those commercially available from Rohm Pharma GmbH, under the tradenames, "EUDRAGIT L" OR "EUDRAGIT S."

Suitable organic solvents include, but are not limited to ethanol, acetone, methylene chloride, ethyl acetate, diethyl ether, hexane, and the like and combinations thereof.

The polymeric mixture may optionally contain other ingredients such as, for example, preservatives, colorants, flavors, plasticizers, detackifiers, defoaming agents, and the like in amounts readily known by one of ordinary skill in the art.

Figure 8A:
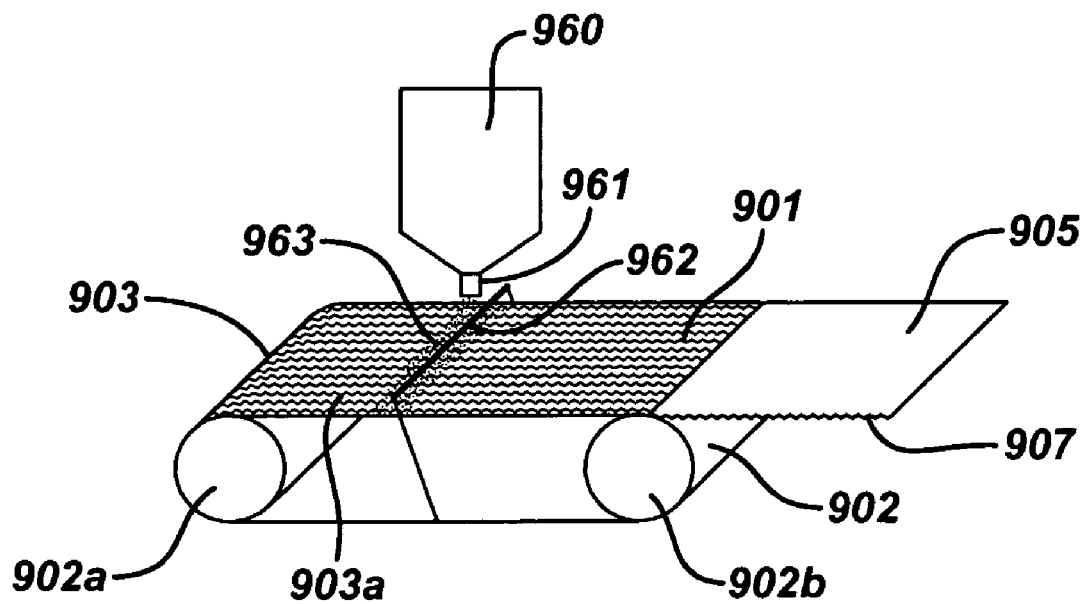
FIG. 8A is a simplified illustration of an apparatus for preparing a film containing a microreliefed surface.

In general, the water insoluble, film forming polymers may be dissolved in the solvent with stirring at ambient temperature such that the solution contains, based upon the total weight of the solution, from about 10% to about 25% of the water insoluble, film forming polymers. The components of the polymeric mixture may be mixed until all components are dissolved and/or dispersed in the solvent. Temperature is not critical. The mixture may then be made into film via any known apparatus for making film. For example, the polymeric mixture may be spread onto a film casting system as illustrated in FIG. 8A, which is comprised of at least two rotating rollers 902a and 902b having a movable belt 903 thereon set to a temperature of about 20° C. to about 50° C. See also Park, W. R. R., *Plastic Film Technology*, Ch. 2 (1969)(FIG. 2.12). In this embodiment, the flowable material 963 may exit a holding tank 960 through a nozzle 961 and be spread across the width of the belt 903 with the assistance of the spreading bar 962. Alternatively (not shown), the spreading bar 962 may be in the form of upper rollers, plates, or the like that produce a substantially uniform, downward pressure on the flowable material. One skilled in the art would readily appreciate that if the film is exposed to a pressure less than atmospheric pressure, then the overall production cycle time should be reduced in order to compensate for the increased rate of evaporation. Alternatively (not shown), the flowable material may be sprayed or spread on to the belt.

The belt 903 advances the flowable material 963, from left to right, at a linear velocity of from about 100 fpm to about 1000 fpm. A microrelief pattern 901 may be engraved into the surface of a supporting change part or mold, such as, for example the belt 903 itself as illustrated in FIG. 8A. After the flowable material 963 is spread onto the belt 903 containing a microrelief pattern 901 on its upper surface 903a and the solvent from the flowable material is permitted to be evaporated therefrom, the exiting material is dried to form a film 905. As the film continuously advances, the lower surface 907 of the exiting film 905 will possess a negative image of the microrelief pattern 901. Examples of such film casting systems are well known in the art and disclosed in, for example, Park, W. R. R., *Plastic Film Technology*, Ch. 2 (1969)(see p. 22).

Figure 8B:
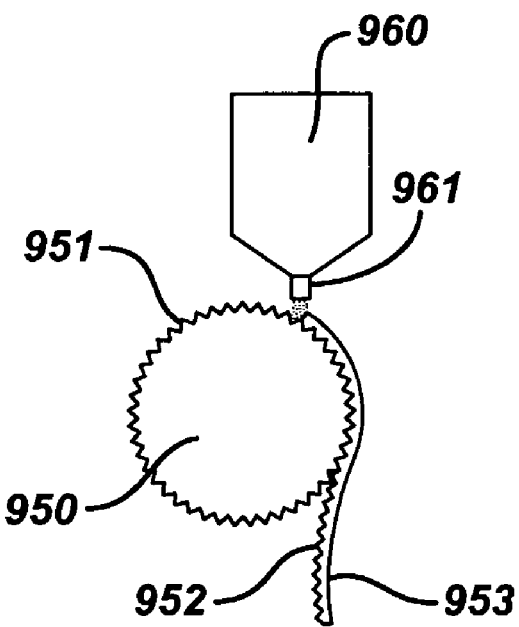
FIG. 8B is a simplified cross sectional view of an alternative apparatus for preparing the same.

In yet another embodiment as shown in FIG. 8B, the polymeric mixture, which is at a temperature equal to or greater than room temperature, may alternatively be dropped onto a roller 950 having an outer surface that possesses a microrelief pattern 951, which is the negative image to that which is formed in the adjacent film surface 952 of the exiting film 953. The roller is set to a temperature sufficient to evaporate the solvent, e.g, typically from about 20° C. to about 50° C., and the tangential velocity of the roller is from about 1 fpm to about 100 fpm.

Although not shown, the polymeric mixture may also alternatively be spread onto a belt or other supporting change part, plate, or mold without microrelief patterns in its surface. A microrelief pattern may then be added to the upper and/or the lower surfaces of the films cast from these belts via methods known in the art such as via stamping or rolling (rotary embossing). Details of these methods are known in the art and disclosed in, for example, U.S. Pat. Nos. 6,349,639; 6,143, 386; and 6,694,872.

The thickness of the resulting films may vary depending upon, for example, the size and detail of the microrelief desired, but generally may vary from about 10 microns to about 500 microns.

The microrelief pattern may be adjusted such that only desired wavelength of light may be reflected therefrom. For example, by adjusting the depth and angle of the ridges and grooves of the microrelief in the molding portion, it may be possible to reflect one color from the resulting microrelief in the film, and with further adjustment of the microrelief in the molding portion, it may be possible to reflect multiple colors from the resulting microrelief in the film.

The resulting films containing microrelief patterns may then be cut to a desired shape and size under ambient conditions via any cutting means known in the art, including but not limited to, millers, shears, knives, or choppers, in order to form microreliefed flakes or "glitter" desired weight and thickness. Optionally, the cut flakes maybe sieved to desired flake size. In this embodiment, it would be possible to collect a multitude of similar flakes having a certain microrelief and a certain size. This is particularly beneficial when a certain color in the wavelength reflected from the microrelief is desired. The resulting flakes may then be added to any media, such as liquids or semi-solids, including but not limited to oral pharmaceutical suspension vehicles such as those disclosed in for example, U.S. Pat. Nos. 5,272,137 and 5,374, 659.

In one embodiment, the resulting microreliefed glitter may be comprised of flakes, which have, for example, different sizes and/or different microrelief patterns, that are dispersed in the media, thereby enabling the light reflected from the flakes' surfaces to appear in a spectrum of colors. By contrast, if only one type and size of microreliefed glitter was dispersed in a media, then the light reflected therefrom would appear to be a more uniform color. The resulting glitter-containing media may then be applied to dosage forms via methods known in the art such as, for example, dip coating or molding. Advantageously, such coatings possess several refractive particles that not only give the dosage form a unique appearance, but are also suitable for human ingestion unlike other, known inorganic interference pigments.

In another embodiment, the flakes may be combined with the above-described powder blend components in order to produce a core with the flakes dispersed throughout the core matrix.

The glitter may be used in a variety of products so long as the glitter remains insoluble therein. Examples of ingestible product uses include those liquids and semi-solids in the fields of pharmaceutical, nutritional, or food. In one embodiment, the glitter may be added to the pharmaceutical powder dosage forms, which may then be added to a pharmaceutically acceptable vehicle. Examples of non-ingestible uses for the glitter include, but are not limited to: 1) cosmetic bases such as body powders, perfumes, blush, eye shadow, and the like; 2) hair care products such as gels, shampoos, conditioners (rinse-out or leave-in), mousses, sprays, and the like; 3) other personal, cosmetic, healthcare, and/or toiletry products such as nail polish, bandages, soap bars, baths, shower gels, wipes, washes, sticks, balms, sachets, pillows, mousses, sprays, lotions, creams, cleansing compositions, powders, oils, bath oils and other bath compositions which may be added to a bath. Personal care compositions may also include, but are not limited to, aerosols, and candles.

Figure 3:
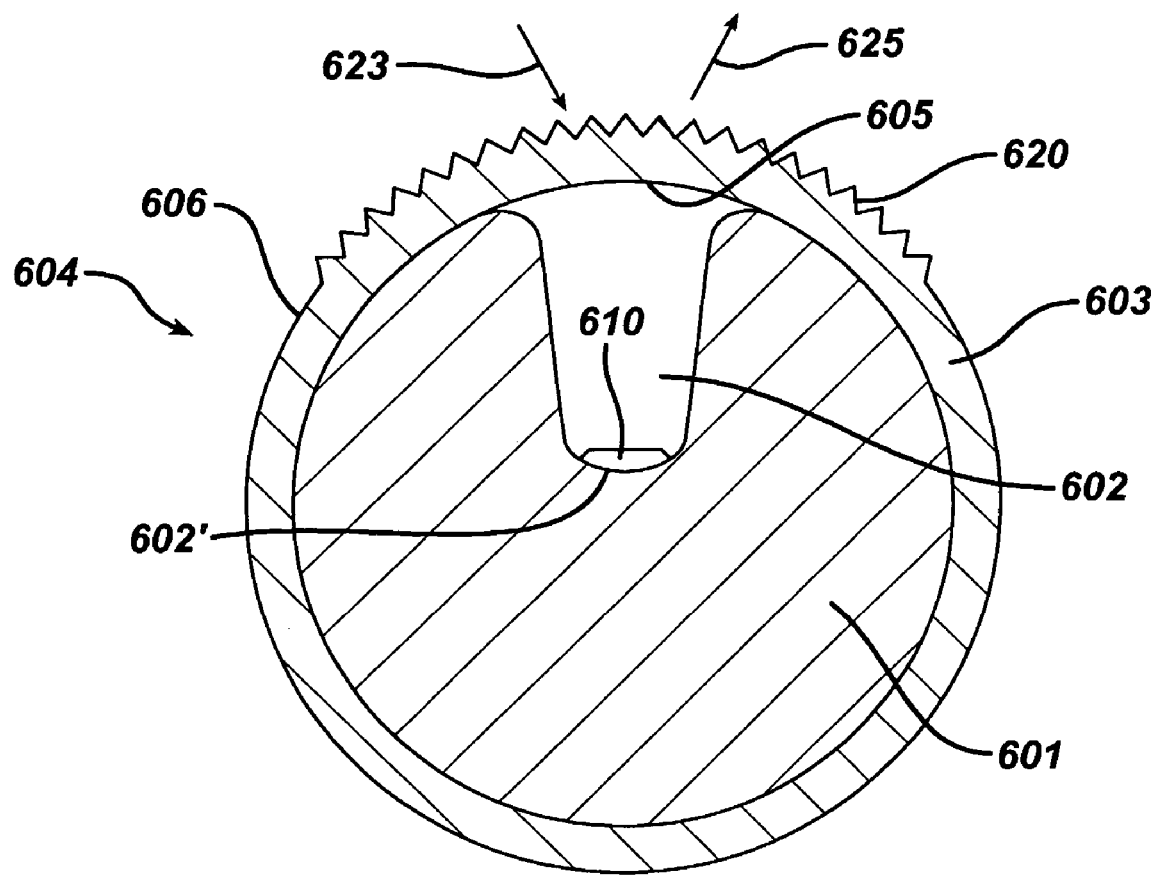
FIG. 3 depicts a cross-sectional view of a dosage form of this invention containing a core with a cavity that is enrobed with a microreliefed film.

Another method for producing a dosage form containing unique visual properties includes the application of lines, or fine dots arranged in a line, in a desired pattern onto the surface of a core, which optionally may be a pattern 610 on the interior surface 602' of a core cavity 602 as shown in FIG. 3, followed by the application of a coating containing a macrorelief pattern thereon.

Any method known in the art for applying lines to a substrate surface may be used such as, for example: a) applying a striped film coating to the dosage form via any of the methods described herein; b) applying a decal or the like containing the striped pattern to the surface of the dosage form; or c) printing strips directly onto the surface of a core via a high resolution printer, such as those commercially available from Harknett, Inc. When the lines are printed on the dosage form as a regularly spaced pattern of lines and overlayed with an identical pattern of lines that is slightly misaligned with the first pattern, an interference-producing, Moiré pattern may be obtained. In one embodiment as shown in FIG. 13, the surface of a dosage form 201 may contain a first printed pattern 202, and a second film 203, which optionally may possess at least one macroreliefed surface, may be overlayed thereon to yield a Moiré pattern effect.

Figure 11A:
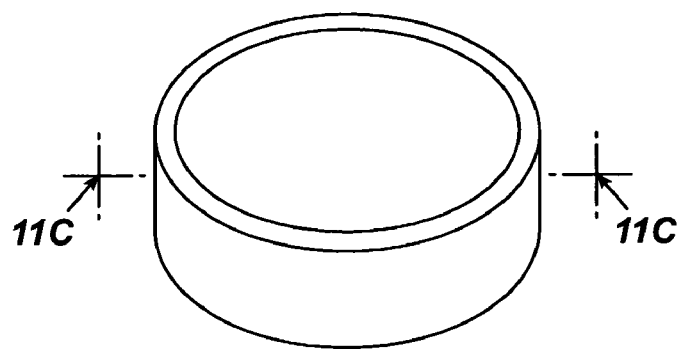
FIGS. 11A-11C are simplified illustrations of the use of lenticular lenses to provide the dosage form with the appearance of one color when viewed from one angle as shown in the perspective view of the dosage form of FIG. 11A, and with the appearance of another color when viewed from another angle as shown in the perspective view of the dosage form in FIG. 11B.
Figure 11B:
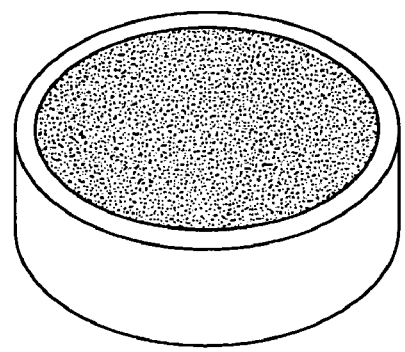
Figure 11C:
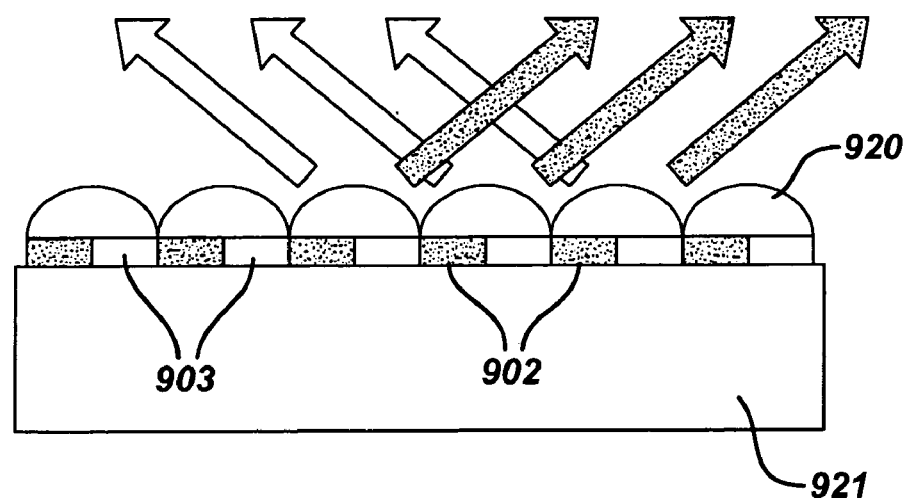

A macrorelief—containing coating may be applied to the striped core surface in a manner similar to those disclosed herein for applying a microreliefed coating to cores. Examples of suitable coatings include, but are not limited to, those comprising gelatin, methacrylic acid and methacrylate ester copolymers, polyvinylpyrrolidone, cellulose acetate, HPMC, polyethylene oxide and polyvinylalcohol copolymers, ethylcellulose, polyvinyl alcohols, and derivatives, and copolymers and mixtures thereof. As a result, when light passes through the lenticules 920 of a microrelief coating on a core 921 as illustrated in FIG. 11, it is reflected from an underlying surface, i.e., e.g., the tablet surface that contains printed information or an image. The lenticule refracts the returning light and magnifies the underlying information or image. The information or image, which underlies the lenticules and is arranged in stripes 902, 903, is appropriately aligned so that all of the stripes for particular information/ image are refracted to the same point in order to create a single image. As the orientation of the lenticular surface is changed in relation to the line of sight by an observer, different image stripes can then be seen as complete images. FIG. 11 illustrates a dosage form having the appearance of two different colors. The dosage form may appear to be one color (FIG. 11A) based upon the refraction of light from a first set of strips 902, and a second color (FIG. 11C) based upon the refraction of light from a second set of strips 903 after the orientation of the lenticular surface is changed.

Figure 10A:
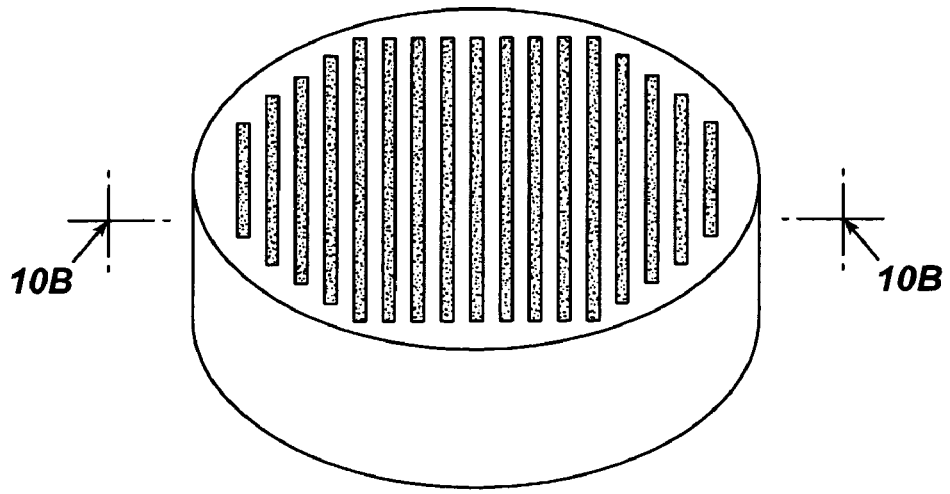
FIG. 10A is an enlarged perspective view of a dosage form having a macrorelief in the form of lenticular lenses in its upper surface.
Figure 10B:
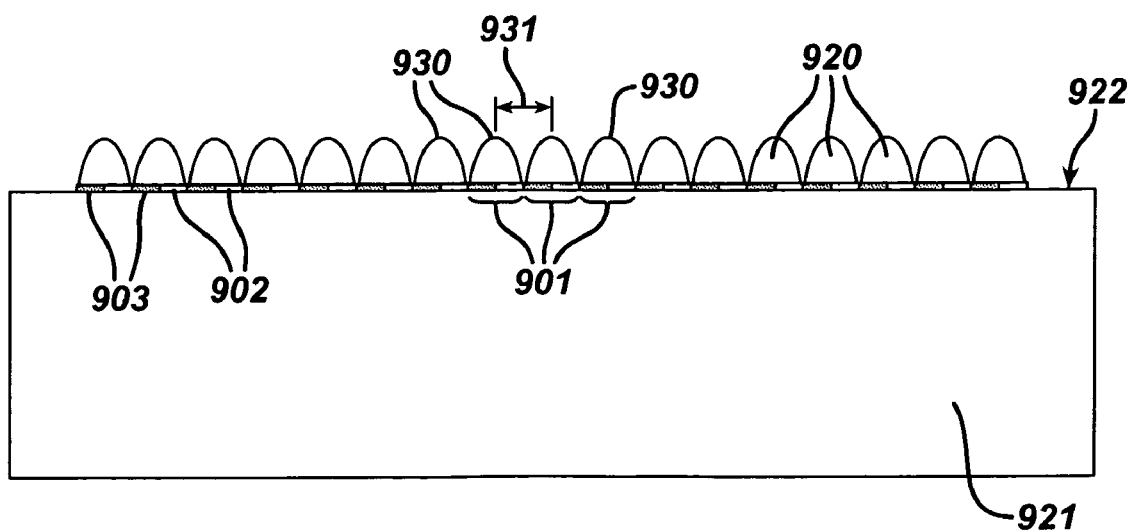
FIG. 10B is an enlarged, side cross-sectional view thereof.

In one embodiment as illustrated in FIG. 10, the printed information may be arranged into a plurality of strips, with at least a first set of strips 902 and a second set of strips 903. At least one of the first set of strips 902 and at least one of the second set of strips 903 are arranged directly on the surface 922 of the core 921, or alternatively on a decal attached to the tablet surface, in an alternating, juxtaposed manner as shown in FIG. 10B, such that a plurality of strip pairs 901 are formed. Each strip pairs 901, respectively, is in substantial vertical alignment beneath one of the plurality of lenticules 920, and is comprised of a first strip 902 and a second strip 903. In this embodiment, the first strips 902 are of one visual distinction, e.g., a first color, and the second strips 903 are of a different visual distinction, e.g., a different color. When an observer looks down directly upon the top surface of the resulting dosage form as shown in FIG. 10A, the dosage form may appear to be striped.

Figure 12A:
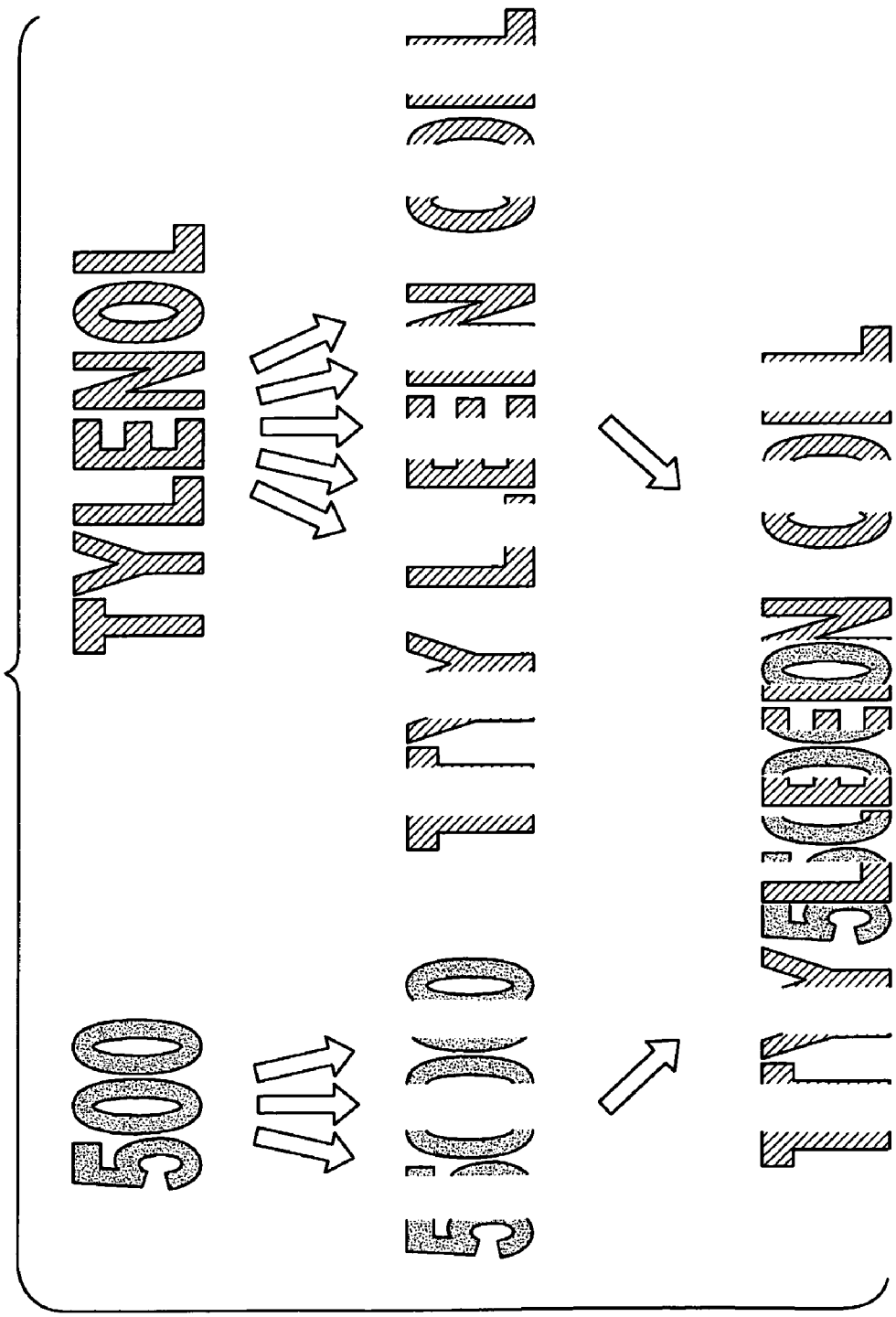
FIG. 12A is a simplified, step-by-step illustration of the process for arranging two exemplary images into strips for use in a lenticular flip image on the dosage form of FIG. 12D.
Figure 12B:
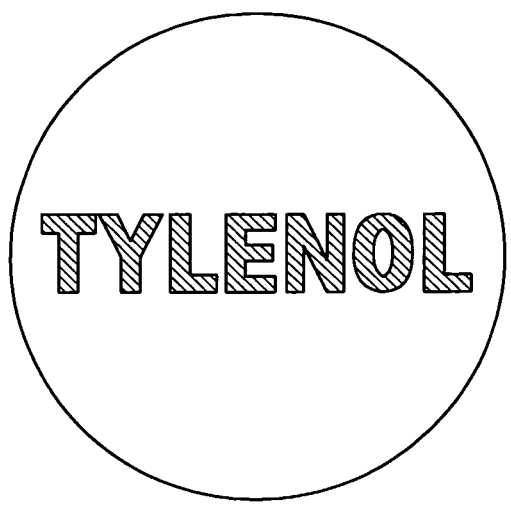
FIG. 12B is a simplified plan view illustration of the dosage form of FIG. 12D having a first lenticular flip image when viewed by an observer from a first angle.
Figure 12C:
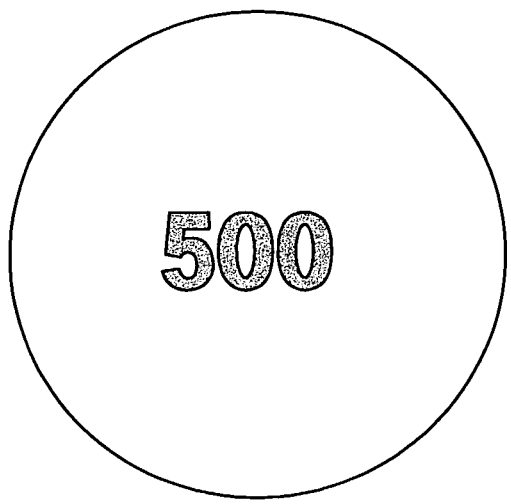
FIG. 12C is a simplified illustration of a plan view of the dosage form of FIG. 12D having a second lenticular flip image when viewed by an observer from a second angle.
Figure 12D:
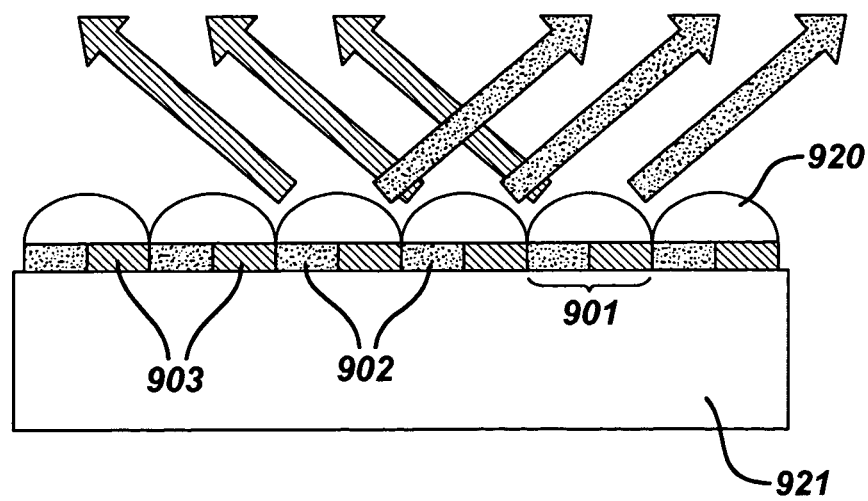
FIG. 12D is an enlarged, cross-sectional side view of a dosage form having a lenticular flip image.
Figure 12E:
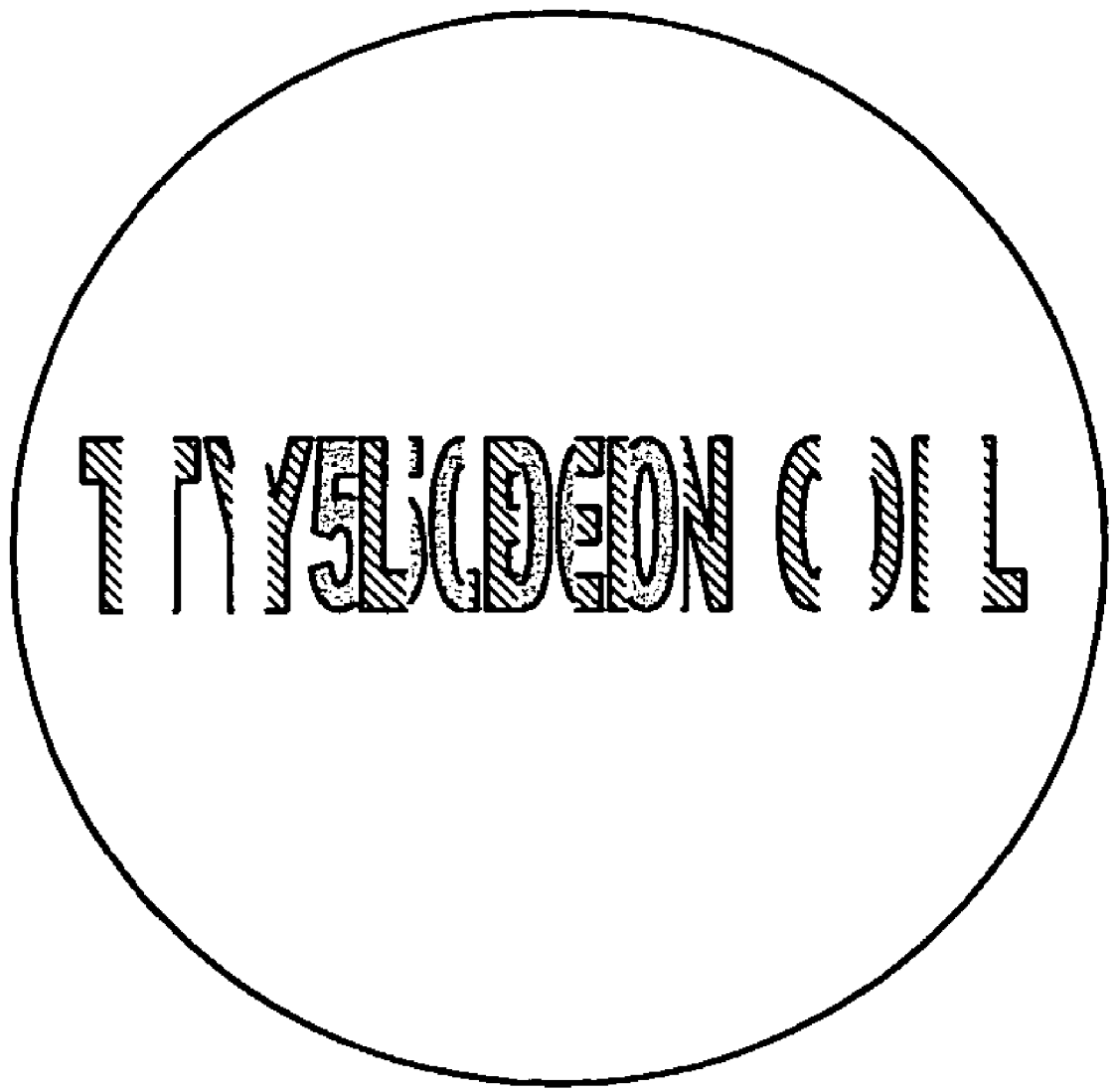
FIG. 12E is a simplified illustration of a plan view of the dosage form of FIG. 12D having two superimposed images when viewed directly on by an observer.

In another embodiment as illustrated in FIG. 12, the surface of the dosage form may either have the appearance of the term, "500," or alternatively the term, "TYLENOL." As shown in FIGS. 12A and 12D, each of these two terms may be divided into a plurality of strips. The strips are then arranged in an alternating manner to form strip pairs 901 on the surface of the core 921. When an observer directly looks down upon the top surface of the resulting dosage form, the dosage form may have the appearance as shown in FIG. 12E. However, as the orientation of the lenticular surface 920 is changed in relation to the line of sight by an observer, the different image stripes can then be seen as one of two complete images, i.e., e.g., as either the "500" (FIG. 12C) or the "TYLENOL" (FIG. 12B).

Each of the plurality of lenticules 902 may have a substantially uniform width of from about 0.1 mm to about 1 mm, and in one embodiment, each of the first strips and the second strips, respectively have a substantially uniform width that is not more than about half the width of each respective lenticule. As shown in FIG. 10B, each lenticule possesses a tip or ridge 930, with a gap 931 between each pair of proximate ridges 930.

The strips may be comprised of any ink or pigment, and optionally may contain an effect pigment. Examples of suitable inks and pigments are those disclosed in, for example, U.S. Pat. Nos. 5,435,840; 5,006,362; and 6,468,561; United States Patent Application No. 20040175463; and WO 2004073582.

Examples of suitable effect pigments include, but are not limited to those providing a nacreous or pearlescent quality to various products and containing titanium oxide and/or iron oxide on a base of mica or flakes of $Al_2O_3$, $SiO_2$, or $TiO_2$, such as those commercially available from Merck KGaA under the tradename, "CANDURIN®." See also WO 2004/073582 A2.

In embodiments wherein the strips are directly printed onto the core surface, the core surface may first be coated with a subcoat, which may be comprised of, for example, any of the aforementioned film forming materials. The subcoating may be applied to the core via any means known in the art such as, for example, spray coating, pan coating, and dip coating. The subcoating should be applied at least to the area selected for printing, and the amount of subcoating used should be, based upon the total weight of the subcoated core, from 0.1 percent to about 10 percent.

In one embodiment, the strips may be directly applied to the core surface while the core is held in an appropriate orientation by a holding means, such as a collet, in order to provide a backing to the core during the printing process. The core then may be fed into an ink-jet printer, a flexoprinter, a silk-screener, or other suitable device that enables the edible ink to be applied onto, and adsorbed by the core surface. Although the color of the ink is not critical, in one embodiment relatively opaque ink may be used to ensure an effective contrast with the surrounding, non-imprinted core areas. In one embodiment, the printed information may be presented in two or more colors.

In embodiments wherein a decal is used, the decal may be comprised of a film such as cellulose acetate, hydroxypropylmethylcellulose, any of the film formers aforementioned, and mixtures thereof, and may be adhered to the core surface by, for example, a known adhesive such as a water and/or alcohol-soluble material or via wet surface tension. Examples of suitable adhesives include, but are not limited to those that are heat-activated, such as starch, vegetable gum or wax. A liquid adhesive may be pre-formed using adhesive in an amount, based upon the total weight of liquid adhesive, from about 1 percent to about 10 percent, and a solvent in an amount appropriate to solubilize the adhesive. Suitable solvents include, but are not limited to, water, alcohol, acetone, and mixtures thereof. In one embodiment, the decal may contain an adhesive on the non-printed surface, then either the adhesive or the surface of the core may be wetted with solvent prior to its application. Alternatively, either the non-printed surface of the adhesive or the surface of the core may be wetted with liquid adhesive prior to application of the decal thereto. The thickness of the decal may vary, but typically will be from about 50 microns to about 250 microns.

In one embodiment, the dosage form may possess a subcoating layer between the core and the decal. The subcoating layer may be comprised of, for example, any of the aforementioned subcoatings.

In one embodiment, the subcoating may be comprised of, based upon the total weight of subcoating, from about 2 percent to about 8 percent, e.g. from about 4 percent to about 6 percent, of a water-soluble cellulose ether; and from about 0.1 percent to about 1 percent of castor oil, as disclosed in U.S. Pat. No. 5,658,589, In another embodiment, the subcoating may be comprised of, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

The subcoating may be applied to the core via any means known in the art such as, for example, spray coating and dip coating. The dried subcoating typically is present in an amount, based upon the dry weight of the core, from about 0 percent to about 5 percent.

An alternative method for producing a dosage form containing unique visual properties includes applying to a dosage form either a film that possesses at least one microreliefed surface or a film containing the aforementioned microreliefed flakes. In one embodiment, cores, which may optionally contain at least one cavity and which may further optionally be comprised of sugar in the form of an amorphous glass, may be enrobed with either of these films via the vacuum forming apparatus and processing conditions disclosed in United States Patent Application No. US 2003/215585A1. The amount of vacuum applied to the film during processing may depend upon, for example, the thickness of the film, the temperature of the film, the depth of the cavity in the dosage form, and the desired amount of air gap in the dosage form, but typically may range from about 0.005 Torr to about 700 Torr. In embodiments using a film having at least one microreliefed surface, the film can touch the cavity-free core surface so long as the microreliefed surface is proximate to the core to form a plurality of airgaps.

FIG. 3 illustrates one embodiment of the resulting dosage form 604l of the present invention, wherein the core 601 is enrobed with a film 603 having a microreliefed surface 620 and an air gap generated between the inner surface of the film 605 and the bottom interior surface 602' of the cavity 602. In an alternative embodiment (not shown), the inner surface 605 or both the inner surface 605 and the exterior surface 606 of the film 603 may possess a microreliefed portion over at least a portion of the cavity 602. As a result, incident light 623 is partially reflected as reflected light 625 at the interface between the bottom surface 605 of the film and the air within the cavity 602, and the microreliefed surface 620 appears brighter than that of similar dosage forms enrobed with microreliefed films but lacking an air gap.

In another embodiment, the interior surface of the cavity 602 may also optionally possess a printed image or pattern 610. In this embodiment, the reflected light 625 could be viewed with the printed pattern 610 in the background, thus resulting in the superimposition of a diffractive image over a printed image. The image or pattern, which may be applied to the dosage form via any of the aforementioned methods, may be in substantial vertical alignment below the structured surface. In one embodiment (not shown), the printed image may be in the form of a plurality of strips, with the gaps of the structured surface not being in substantial vertical alignment with the strips.

One of the advantages of this invention is that in the embodiments wherein the dosage forms have an inlaid portion, the inlaid portion may not only have a complex geometry or pattern, but is the dosage form is further rendered unique by virtue of the microrelief pattern within the inlaid portion. For example, inserts or inlaid portions previously disclosed in the prior art typically have been limited to simple shapes, e.g. shapes having circular cross-sections. Using prior art techniques, it would be extremely difficult to press fit a complex logo, for example an intagliation that causes or requires discontinuities in the surface of the substrate, core, or first portion into which it must fit. However, because the insert or inlaid portion of the present invention is obtained using a flowable material, it may be used to fill any depression in any shape or continuous pattern, or even a discontinuous pattern if multiple nozzles are employed. The resulting dosage form is further differentiable from other dosage forms due to the unique micrograph inserted into the inlaid portion.

Another particular advantage of the embodiments of the present invention wherein the dosage form has an inlaid portion is that the inserts or inlaid portions may be larger in cross-section (in at least one portion) than the cavity, which contains the insert or inlaid portion. For example, in one embodiment in which a second molded portion is inlaid into one or more cavities in the exterior surface of a first portion of the dosage form, the area of at least one cross-section of the second molded inlaid portion is greater than the cross-sectional area of the cavity at the surface of the first portion. In contrast, in the prior art an insert must be no larger in cross-section than the opening of the cavity, which contains the insert. This may also be expressed in terms of the "draft angle" of the insert or inlaid portion. As used herein, the term "draft angle" refers to the angle defined by the side wall of the cavity and a line perpendicular to the face of the first portion, as described for example in Rosato et al., *Injection Molding Handbook*, pp. 601-04, (2d ed. 1995), the disclosure of which is incorporated herein by reference.

Advantageously, the dosage forms produced in accordance with the embodiments of the present invention may possess a unique logo, diffractive color pattern or other product identifying appearance, which not only help the user to identify the brand but also help to control and detect counterfeit dosage forms.

Further, the dosage forms may also advantageously provide unique visual and color effects and images to dosage forms, as well as to other toiletry, cosmetic, healthcare, and foodstuffs, such that they possess a unique appearance without the use of inedible metal, dye, color, and ink pigments. In one embodiment, the brightness of the logo or diffractive color pattern of the microrelief on a dosage form may further be enhanced by using a core having a shiny light colored, e.g. white, reflective surface. As used herein, "shiny" or "highly glossy" means that the core, substrate, or dosage form possesses a surface gloss of at least 200, for example between about 200 to about 300. "Surface gloss," as used herein, refers to the amount of light reflectance as measured at a 60 degree incident angle using the method set forth in Example 7 of United States Patent Application Publication No.20030072731. For example, in embodiments wherein a highly glossy effect is desired, the core may be comprised of a polyol such as sorbitol, xylitol, mannitol, and the like, or may be coated with a subcoating comprised of, for example, pullulan and other subcoatings as disclosed in U.S. Pat. Nos. 6,248,391; 6,274,162; 5,468,561; 6,448,323; 6,183,808; and 5,662,732; and WO 2004 073582.

In addition, the dosage forms of the present invention beneficially may be made with apparatus and processes that are not only economical to use, but also are compatible with current production techniques.

This invention will be further illustrated by the following examples, which are not meant to limit the invention in any way.

EXAMPLES

Example 1

Compressed Acetaminophen Tablets with Diffractive Intagliation

Acetaminophen tablets having the formula set forth in Table A below are compressed on a rotary tablet press. The tablet press is equipped with compression tooling that is designed to deboss the upper surface of the pressed tablet with the letter "Y." See FIGS. 5A and 5B. The compression tooling is keyed such that the orientation of the debossed lettering is the same for all tablets and is in proper alignment with the molding cavities of the injection molding apparatus.

TABLE A

| Debossed Tablet Core Formulation | |
| --- | --- |
| Ingredient | mg/tablet core |
| Paracetamol DC273N (P.G.S.) - US* | 529.1 |
| Sodium Starch Glycolate NF-Explotab | 25.0 |
| Magnesium Stearate NF | 2.0 |
| TOTAL CORE | 556.1 |

*granulation available from Mallinckrodt

Once formed, the tablet containing the debossed "Y" in its surface is transferred to an injection molding apparatus, where the tablet is placed in a mold cavity such that the portion of the debossed tablet bearing the letter "Y" is located under an injector tip. The surface of the mold cavity that is located above the debossed tablet face contains an insert, which also bears the letter "Y" and is in vertical alignment with the debossed "Y" in the tablet face. The area within the letter "Y" on the insert is etched with a diffractive relief pattern having about 500 lines per mm.

An aqueous gelatin solution (35% solids) at 50° C. is then injected through the injector tip of the molding apparatus into the void of the debossed "Y" in the tablet surface. The gelatin is permitted to fill the void until the gelatin is contacts the surface of the mold bearing the diffractive relief pattern, which is maintained at a temperature of about 10° C. Upon cooling to room temperature in the mold, the gelatin solution forms a gel that fills the void in the tablet and, along its exterior surface, assumes the reverse image of the diffractive relief pattern in the mold.

During drying, the gelatin shrinks vertically, e.g., by about 65% and laterally, e.g., by about 5%. In order to compensate for this shrinkage, the diffractive relief pattern molded into the wet gelatin is sized to be about 65% larger in the vertical dimension and about 5% larger in the horizontal dimension than the dimensions of the pattern in the final dried product. The resulting dried product has a diffractive grating of 500 lines or grooves per millimeter, and the diffractive pattern etched into the surface of the mold is a negative pattern having 476 lines or grooves per millimeter. Likewise in the vertical dimension, the resulting dried product has a diffractive grating of about ⅔ microns in height, and the diffractive pattern etched into the surface of the mold is a negative pattern having a vertical dimension of about 2 microns.

Example 2

Compressed Acetaminophen Core having a Surface Microrelief

Acetaminophen tablets having the formulation set forth below in Table B are prepared using a rotary tablet press of Example 1.

TABLE B

| Tablet Core Formulation | |
|---|---|
| Ingredient | mg/tablet core |
| Paracetamol DC273N (P.G.S.) - US* | 400.0 |
| Microcrystalline Wax** | 150.0 |
| Magnesium Stearate NF | 2.0 |
| TOTAL CORE | 552.0 |

*commercially available from Mallinckrodt
**plastically deforming agent

The upper punch face of the tablet press is engraved with a series of parallel lines of about 500 lines per millimeter to yield a diffractive pattern in the shape of the letter "Y". After compression, the resulting tablet surface has a coating of the plastically deforming agent bearing a negative impression of the microrelief.

This Example shows that during compression of the core granulation, the plastically deforming agent at the surface of the tablet flows under pressure and molds to the contour of the micro relief. After compression, the flow of the plastically deforming agent ceases, which then leaves the tablet surface with a coating of the plastically deforming agent bearing a negative impression of the punch face micro relief.

Example 3

Coated, Compressed Acetaminophen Core having a Surface Microrelief

Compressed tablets, which are made in accordance with the procedure set forth in Example 2, are warmed to a temperature of about 30° C., then thinly coated with a poly (butyl methacrylate, (2-dimethylaminoethyl)methacrylate, methyl methacrylate) polymeric dispersion, which is commercially available from Rohm Pharma GmbH under the tradename, "Eudragit EPO" via a spray gun. Spray rate, inlet air quantity and inlet air temperature are adjusted in such a way that spraying can be performed continuously. The tablets are maintained at a temperature of about 25° C. to about 35° C. during coating. The coating weight gained is, based upon the original weight of the uncoated compressed tablet, from about 2 percent to about 5 percent.

Example 4

Coated Tablets bearing a Microrelief and an Air Gap between the Coating Layer and the Tablet Surface.

Acetaminophen tablets having the formulation set forth below in Table C are prepared using the rotary tablet press of Example 1.

TABLE C

| Tablet Core Formulation | |
|---|---|
| Ingredient | mg/tablet core |
| Paracetamol DC273N (P.G.S.) - US* | 529.1 |
| Avicel PH 101 | 200.0 |
| Magnesium Stearate NF | 2.0 |
| TOTAL CORE | 731.1 |

*commercially available from Mallinckrodt

The resulting tablets are then transferred to a mold cavity within an injection molder apparatus. The upper inner face of the mold cavity contains an insert, which is etched with a diffractive relief pattern in the form of a "Y." The diffractive relief pattern consists of parallel grooves of about 500 grooves per millimeter.

A saturated polyglycolized glyceride waxy thermoplastic material available from Gattefosse under the tradename, "Gelucire 39/01," which has a melting temperature of about 39° C., is injected as a liquid at a temperature of about 50° C. into the mold and onto the surface of the tablet therein. The liquid thermoplastic material is solidified in the mold, which is set at a temperature of about 20° C. As a result, a coating is formed on the tablet bearing the reverse image of the diffractive relief pattern of the mold surface.

After the tablets are then warmed to a temperature of about 30° C., the tablets are then thinly coated with a poly (butyl methacrylate, (2-dimethylaminoethyl)methacrylate, methyl methacrylate) polymeric dispersion, which is commercially available from Rohm Pharma GmbH under the tradename, "Eudragit EPO" via a spray gun. Spray rate, inlet air quantity and inlet air temperature are adjusted in such a way that spraying can be performed continuously. The tablets are maintained at a temperature of about 25° C. to about 35° C.

during coating. The coating weight gained is, based upon the original weight of the uncoated compressed tablet, is about 10 percent.

The tablets are then heated to about 50° C. for a time sufficient to melt the waxy, Gelucire layer, which is substantially absorbed by the tablet core. As a result, an air gap is formed between the and core and the Eudragit layer. The inner surface of the Eudragit layer, which faces the tablet core surface, retains the reverse image of the diffractive relief pattern formerly in the Gelucire layer.

Example 5

Tablet Coating Containing Diffractive Flakes

A. Method for Preparing Microrelief Films Via Solution Casting:

A cellulose acetate (CA) polymer solution at 15% w/w solids in acetone is cast into a film over a steel belt supporting substrate. The upper surface of the substrate contains a diffractive microrelief having about 500 lines or grooves per millimeter. After evaporating the solvent away, the dried CA film, which is about 1 micron to about 5 microns in thickness and bears the microrelief pattern on its lower film surface, is peeled off of the substrate then cut/chopped to the desired size and shape of the flakes, i.e., 0.5 mm$^2$.

B. Method For Coating Tablets With Gelatin Solution Containing Microrelief Flakes:

About 5% w/w of the CA micro relief film flakes produced in accordance with Example 5A above are dispersed into a 35% w/w gelatin aqueous solution. The resulting gelatin solution is then dip coated onto the tablets produced in accordance with the procedure of Example 1. The coating weight gained is, based upon the original weight of the uncoated tablet, about 5.3% percent. The resulting coating on the tablet contains light diffractive flakes that giving a sparkly appearance to the resulting dosage form.

Example 6a

Color Shifting Tablet by Edible Lenticular Coating.

Acetaminophen tablets having the formulation set forth below in Table D are prepared using the rotary tablet press of Example 1. The tablet surface or portion of the resulting tablets is sufficiently smooth to allow for fine printing thereon.

TABLE D

| Tablet Core Formulation | |
|---|---|
| Ingredient | mg/tablet core |
| Paracetamol DC273N (P.G.S.) - US | 529.1 |
| Sodium Starch Glycolate NF-Explotab | 25.0 |
| Magnesium Stearate NF | 2.0 |
| TOTAL CORE | 556.1 |

The resulting, flat-faced tablets are then transported to a tablet printer having a resolution of at least 0.15 mm. One face of the tablet is then printed with a series of alternating red and yellow strips 0.15 mm in width to form a lenticular split image/pattern.

The printed tablets are then positioned in a molding apparatus of Example 4 such that the colored lines are in parallel alignment with the lenticular grooves located above in the mold cavity. The grooves in the mold cavity are about 0.315 mm wide and about 0.225 mm in height in order to compensate for shrinkage of a 35% w/w gelatin solution on the final dried dosage form.

The mold then closes over the tablet, and a 35 w/w % gelatin solution is then injected and solidified over the printed tablet. After the tablet is removed from the mold and dried, the gelatin coating forms an edible lenticular lens layer on the tablet surface. The final, dried dosage form displays a lenticular split image which, in this case, is a flip image that transitions between red and yellow when the tablet is viewed at different angles.

Example 6b

Flip Image Tablet Logo and Dose using Edible Lenticular Coating.

Acetaminophen tablets having the formulation set forth below in Table E are prepared using the rotary tablet press of Example 1. The tablet surface or portion of the resulting tablets is sufficiently smooth to allow for fine printing thereon.

TABLE E

| Tablet Core Formulation | |
|---|---|
| Ingredient | mg/tablet core |
| Paracetamol DC273N (P.G.S.) - US | 529.1 |
| Sodium Starch Glycolate NF-Explotab | 25.0 |
| Magnesium Stearate NF | 2.0 |
| TOTAL CORE | 556.1 |

The resulting, flat-faced tablets are then transported to a tablet printer having a resolution of at least 0.15 mm. The tablet logo and dosage strength are then printed as a lenticular split image on the tablet face surface. One face of the tablet is then printed with a series of alternating red and blue strips, each of which are about 0.15 mm in width, of the words, "TYLENOL" and "500" superimposed in the form of a lenticular split image.

The printed tablets are then positioned in a molding apparatus of Example 4 such that the colored lines are in parallel alignment with the lenticular grooves located above in the mold cavity. The grooves in the mold cavity are about 0.315 mm wide and about 0.225 mm in height in order to compensate for shrinkage of a 35% w/w gelatin solution on the final dried dosage form.

The mold then closes over the tablet, and the gelatin solution is then injected and solidified over the printed tablet. After the tablet is removed from the mold and dried, the gelatin coating forms an edible lenticular lens layer on the tablet surface. The final, dried dosage form displays a lenticular split image which, in this case, is a flip image that transitions between the words "TYLENOL" in red and "500" in blue when the tablet is viewed at different angles.

Although this invention has been illustrated by reference to specific embodiments, it will be apparent to those skilled in the art that various changes and modifications may be made which clearly fall within the scope of this invention.

The invention claimed is:
1. A dosage form comprised of:
a) a core, wherein the core comprises a pharmaceutically active agent; and b) an outer layer comprised of a carrier and the composition comprised of polymeric film flakes having at least one surface wherein the polymeric film flakes possess a microrelief on the at least one surface and wherein the microrelief is a high resolution diffraction grating or dovid.

2. The dosage form of claim 1, wherein the outer layer is further comprised of a polymeric matrix containing at least one polymer in a substantially amorphous form.

3. The dosage form of claim 1, wherein the core further comprises a pharmaceutically active agent.

4. The dosage form of claim 1, wherein the microrelief is a high resolution diffraction grating.

5. The dosage form of claim 1, wherein the microrelief is a dovid.

6. The dosage form of claim 2, wherein the core further comprises a pharmaceutically active agent.

7. The dosage form of claim 2, wherein the microrelief is a high resolution diffraction grating.

8. The dosage form of claim 3, wherein the microrelief is a high resolution diffraction grating.

9. The dosage form of claim 6, wherein the microrelief is a high resolution diffraction grating.

10. The dosage form of claim 2, wherein the microrelief is a dovid.

11. The dosage form of claim 3, wherein the microrelief is a dovid.

12. The dosage form of claim 6, wherein the microrelief is a dovid.

13. The dosage form of claim 5, wherein the dovid is a hologram.

14. The dosage form of claim 10, wherein the dovid is a hologram.

15. The dosage form of claim 11, wherein the dovid is a hologram.

16. The dosage form of claim 12, wherein the dovid is a hologram.

17. The dosage form of claim 13, wherein the dovid is a hologram.

* * * * *